(12) United States Patent
Dodge et al.

(10) Patent No.: US 10,744,210 B2
(45) Date of Patent: Aug. 18, 2020

(54) GENE THERAPY FOR SPINAL CORD DISORDERS

(75) Inventors: James Dodge, Worcester, MA (US); Lamya Shihabuddin, Brighton, MA (US); Marco Passini, Shrewsbury, MA (US); Seng H. Cheng, Wellesley, MA (US); Catherine O'Riordan, Waban, MA (US)

(73) Assignee: GENZYME CORPORATION, Cambridge, MA (US)

( * ) Notice: Subject to any disclaimer, the term of this patent is extended or adjusted under 35 U.S.C. 154(b) by 20 days.

(21) Appl. No.: 11/934,148

(22) Filed: Nov. 2, 2007

(65) Prior Publication Data

US 2009/0069261 A1 Mar. 12, 2009

Related U.S. Application Data

(63) Continuation of application No. PCT/US2006/016943, filed on May 2, 2006.

(60) Provisional application No. 60/677,213, filed on May 2, 2005, provisional application No. 60/790,217, filed on Apr. 8, 2006.

(51) Int. Cl.
*A61K 48/00* (2006.01)
*C12N 15/864* (2006.01)
*C07K 14/475* (2006.01)

(52) U.S. Cl.
CPC ........ *A61K 48/0075* (2013.01); *C07K 14/475* (2013.01); *C12N 15/8645* (2013.01); *C12N 2750/14041* (2013.01); *C12N 2799/025* (2013.01)

(58) Field of Classification Search
CPC ............. A61K 48/0075; C07K 14/475; C12N 15/8645; C12N 2750/14041; C12N 2799/025
USPC ..................................... 514/44 R; 424/199.1
See application file for complete search history.

(56) References Cited

U.S. PATENT DOCUMENTS

| | | | |
|---|---|---|---|
| 5,658,776 A | 8/1997 | Flotte et al. | |
| 5,672,344 A | 9/1997 | Kelley et al. | |
| 5,773,278 A | 6/1998 | Schuchman et al. | |
| 6,042,576 A | 3/2000 | DeVries | |
| 6,180,613 B1 | 1/2001 | Kaplitt et al. | |
| 6,503,888 B1 | 1/2003 | Kaplitt et al. | |
| 6,541,218 B1 | 4/2003 | Schuchman et al. | |
| 6,544,785 B1 | 4/2003 | Palese et al. | |
| 6,667,174 B2 | 12/2003 | Yew | |
| 2003/0118552 A1 | 6/2003 | Kasper et al. | |
| 2003/0118556 A1* | 6/2003 | Kaspar et al. | 424/93.2 |
| 2003/0165481 A1 | 9/2003 | Hersh | |
| 2004/0258666 A1* | 12/2004 | Passini et al. | 424/93.2 |
| 2008/0292593 A1 | 11/2008 | Passini et al. | |
| 2009/0069261 A1 | 3/2009 | Dodge et al. | |
| 2009/0117156 A1 | 5/2009 | Passini et al. | |

FOREIGN PATENT DOCUMENTS

| | | |
|---|---|---|
| CN | 1575340 A | 2/2005 |
| EP | 0130166 | 2/1985 |
| EP | 1 879 625 B1 | 12/2010 |
| WO | WO-95/00655 A1 | 1/1995 |
| WO | WO-95/11984 A2 | 5/1995 |
| WO | WO-95/11984 A3 | 5/1995 |
| WO | WO-95/27071 A2 | 10/1995 |
| WO | WO-95/27071 A3 | 10/1995 |
| WO | WO-01/36603 A2 | 5/2001 |
| WO | WO-01/36603 A3 | 5/2001 |
| WO | WO-03/055983 A2 | 7/2003 |
| WO | WO-03/055983 A3 | 7/2003 |
| WO | WO-2004/098648 A1 | 11/2004 |

OTHER PUBLICATIONS

Burger et al. (2004) Mol. Ther., vol. 10, 302-317.*
Passini et al. (2003) J. Virol., vol. 77(12), 7034-7040.*
PCT Int. Search Report, Jul. 5, 2007, Genzyme Corporation.
Boillee et al., "Gene therapy for ALS delivers", Trends in Neuroscience, Elsevier, Amsterdam, NL, vol. 27, No. 5, Jan. 1, 2004, pp. 235-238.
Kaemmerer, W. F. et al., "In Vivo transduction of cerebellar Purkinje cells using, adeno-associated virus vectors", Molecular Therapy, vol. 2, No. 5, 2000, pp. 446-457.
EP Search Report, Feb. 18, 2009, Genzyme Corporation.
Auricchio, A. et al. (Dec. 15, 2001). "Exchange of Surface Proteins Impacts on Viral Vector Cellular Specificity and Transduction Characteristics: The Retina as a Model," *Hum. Mol. Genet.* 10(26):3075-3081.
Ausubel, F.M. et al. (1987). *Current Procedure in Molecuarl Biology,* John Wiley & Sons, New York, New York, seven pages, (Table of Contents Only.).
Azzouz, M. et al. (May 27, 2004). "VEGF Delivery With Retrogradely Transported Lentivector Prolongs Survival in a Mouse ALS Model," *Nature* 429:413-417.
Bartlett, J.S. et al. (May 20, 1998) "Selective and Rapid Uptake of Adeno-Associated Virus Type 2 in Brain," *Hum. Gene Ther.* 9:1181-1186.

(Continued)

*Primary Examiner* — Anne Marie S Wehbe
(74) *Attorney, Agent, or Firm* — Morrison & Foerster LLP

(57) ABSTRACT

This disclosure provides methods and compositions for treating disorders or injuries that affect motor function and control in a subject. In one aspect, the invention provides a method to deliver a transgene to a subject's spinal cord by administering a recombinant neurotropic viral vector containing the transgene. The viral vector delivers the transgene to a region of the deep cerebellar nuclei region of the brain. Also provided are compositions and methods to deliver a transgene to a subject's spinal cord by administering a recombinant neurotropic viral vector containing the transgene to the motor cortex region of the subject's brain.

10 Claims, 23 Drawing Sheets

Specification includes a Sequence Listing.

(56) References Cited

OTHER PUBLICATIONS

Bosch, A. et al. (Jan. 2000). "Long-Term and Significant Correction of Brain Lesions in Adult Mucopolysaccharidossi Type VII Mice Using Recombinant AAV Vectors," *Molecular Therapy* 1(1):63-70.
Breakefield, X.O. et al. (Mar. 1991). "Herpes Simplex Virus for Gene Delivery to Neurons," *New Biol.* 3(3):203-218.
Chamberlin, N.L. et al. (May 18, 1998). "Recombinant Adeno-Associated Virus Vector: Use for Transgene Expression and Anterograde Tract Tracing in the CNS," *Brain Res.* 793:169-175.
Clark, K.R. et al. (Apr. 10, 1999). "Highly Purified Recombinant Adeno-Associated Virus Vectors are Biologically Active and Free of Detectable Helper and Wild-Type Viruses," *Hum. Gene Ther.* 10:1031-1039.
Datto, J. et al. (Nov. 2002). "Distribution of AAV-1 GFP With Respect to Time, Distance, Traveled and Expression Following Injection to the Midbrain," *Meeting for Society for Neuroscience*, Orlando, Florida, Nov. 3-7, 2002, Abstract No. 623.4, two pages.
Davidson, B.L. et al. (May 2003). "Viral Vectors for Gene Delivery to the Nervous System," *Nat. Rev.* 4:353-364.
Defalco, J. et al. (Mar. 30, 2001). "Virus-Assisted Mapping of Neural Inputs to a Feeding Center in the Hypothalamus," *Science* 291:2608-2613.
Donello, J.E. et al. (Jun. 1998). "Woodchuck Hepatitis Virus Contains a Triparttite Posttranscriptional Regulatory Element," *J. Virol.* 72(6):5085-5092.
Elbashir, S.M. et al. (Jan. 15, 2001). "RNA Interference is Mediated by 21- and 22-Nucleotide RNAs," *Genes Dev.* 15(2):188-200.
Fisher, K.J. et al. (Jan. 1996). "Transduction with Recombinant Adeno-Associated Virus for Gene Therapy is Limited by Leading-Strand Synthesis," *J. Virol.* 70(1):520-532.
Gal, A.E. et al. (Sep. 25, 1975). "A Practical Chromogenic Procedure for the Detection of Homozygotes and Heterozygous Carriers of Niemann-Pick Disease," *N. Engl. J. Med.* 293(13):632-636.
Gao, G.P. et al. (Sep. 3, 2002). "Novel Adeno-Associated Viruses From Rhesus Monkeys as Vectors for Human Gene Therapy," *Proc. Natl. Acad. Sci. U.S.A.* 99(18):11854-11859.
Gonatas, N.K. et al. (Mar. 1992). "Fragmentation of the Golgi Apparatus of Motor Neurons in Amyotrophic Lateral Sclerosis," *Am. J. Pathol.* 140(3):731-737.
Haberman, R.P. et al. (1998). "Inducible Long-Term Gene Expression in Brain With Adeno-Associated Virus Gene Transfer," *Gene Ther.* 5:1604-1611.
Harlow, E. et al. eds. (1988). *Antibodies, A Laboratory Manual, and Animal Cell Culture*, Freshney, R.I. ed., Cold Spring Harbor Laboratory, pp. iii-ix, (Table of Contents Only.).
Hermonat, P.L. et al. (Oct. 1984). "Use of Adeno-Associated Virus as a Mammalian DNA Cloning Vector: Transduction of Neomycin Resistance Into Mammalian Tissue Culture Cells," *Proc. Natl. Acad. Sci. U.S.A.* 81:6466-6470.
Horinouchi, K. et al. (Jul. 1995). "Acid Sphingomyelinase Deficient Mice: A Model of Types A and B Niemann-Pick Disease," *Nature Genetics* 10:288-293.
Iwata, N. et al. (Feb. 2000). "Identification of the Major $A\beta_{1-42}$-Degrading Catabolic Pathway in Brain Parenchyma: Suppression Leads to Biochemical and Pathological Deposition," *Nat. Med.* 6(2):143-150.
Iwata, N. et al. (Jan. 28, 2004). "Presynaptic Localization of Neprilysin Contributes to Efficient Clearance of Amyloid-βPeptide in Mouse Brain," *J. Neurosci.* 24(4):991-998.
Janson, C. et al. (Jul. 20, 2002). "Clinical Protocol. Gene therapy of Canavan Disease: AAV-2 Vector for Neurosurgical Delivery of Aspartoacylase Gene (ASPA) to the Human Brain," *Hum. Gene Ther.* 13:1391-1412.
Jeyakumar, M. et al. (Oct. 2002). "Glycosphingolipid Lysosomal Storage Diseases: Therapy and Pathogenesis," *Neuropath. Appl. Neurobiol.* 28:343-357.
Jin, H.K. et al. (May 2002). "Intracerebral Transplantation of Mesenchymal Stem Cells into Acid Sphingomyelinase-Deficient Mice Delays the Onset of Neurological Abnormalities and Extends Their Life Span," *J. Clin. Invest.* 109:1183-1191.

Kandel et al. (1991). *Principles of Neural Science*, 4th ed., McGraw-Hill, New York, New York, pp. ix-xi (Table of Contents Only.).
Kanemitsu, H. et al. (Oct. 23, 2003). "Human Neprilysin is Capable of Degrading Amyloid β Peptide not Only in the Monomeric Form but Also the Pathological Oligomeric Form," *Neurosci. Lett.* 350:113-116.
Kaplitt, M.G. et al. (Oct. 1994). "Long-Term Gene Expression and Phenotypic Correction Using Adeno-Associated Virus Vectors in the Mammalian Brain," *Nat. Genet.* 8:148-154.
Kaspar, B.K. et al. (Jan. 2002). "Targeted Retrograde Gene Delivery for Neuronal Protection," *Mol. Ther.* 5(1):50-56.
Kaspar, B.K. et al. (Aug. 3, 2003). "Retrograde Viral Delivery of IGF-1 Prolongs Survival in a Mouse ALS Model," *Science* 301:839-842.
Klein, R.L. et al. (Apr. 1998). "Neuron-Specific Transduction in the Rat Septohippocampal or Nigrostriatal Pathway by Recombinant Adeno-Associated Virus Vectors," *Exp. Neurol.* 150:183-194.
Kurreck, J. (Apr. 2003). "Antisense Technologies: Improvement Through Novel Chemical Modifications," *J. Eur. Biochem.* 270:1628-1644.
Lebkowski, J.S. et al. (Oct. 1988)."Adeno-Associated Virus: A Vector System for Efficient Introduction and Integration of DNA Into a Variety of Mammalian Cell Types," *Mol. Cell. Biol.* 8(10):3988-3996.
Leventhal, A.R. et al. (Nov. 30, 2001, e-pub. Sep. 28, 2001). "Acid Sphingomyelinase-Deficient Macrophages Have Defective Cholesterol Trafficking and Efflux," *J. Biol. Chem.* 276(48):44976-44983.
Lindsay, R.M. (1994). "Neurotrophic Growth Factors and Neurodegenerative Diseases: Therapeutic Potential of the Neurotrophins and Ciliary Neurotrophic Factor," *Neurobiol. Aging* 15(2):249-251.
Liu, Y. et al. (2002). "High Level of Transduction of Mammalian Brian by Adeno-Associated Type 1 Virus Vector," *Society for Neuroscience*, Orlando, Flordia, Nov. 3-7, 2002, Abstract No. 902.2, 2 pages.
Machida, C.A. ed. (2003). *Viral Vectors for gene Therapy: Methods and Protocols*, Humana Press, pp. vii-x, (Table of Contents Only.).
Mai, J.K. et al. (1997). *Atlas of the Human Brain*, Academic Press, San Diego, CA, pp. vii-viii, (Table of Contents Only).
Mandel. R.J. et al. (Jun. 1, 1998). "Characterization of Intrastriatal Recombinant Adeno-Associated Virus-Mediated Gene Transfer of Human Tyrosine Hydroxylase and Human GTP-Cyclohydrolase I in a Rat Model of Parkinson's Disease," *J. Neurosci.* 18(11):4271-4284.
Mandel, R.J. et al. (2000). "Intracerebral Gene Transfer using Viral Vectors," *Neuromethods* 36:103-130.
Marr, R.A et al. (Mar. 15, 2003). "Neprilysin Gene Transfer Reduces Human Amyloid Pathology in Transgenic Mice," *J. Neurosci.* 23(6):1992-1996.
Marr, R.A. et al. (2004). "Neprilysin Regulates Amyloid β Peptide Levels," *J. Mol. Neurosci.* 22:5-11.
Matsushita, M. et al. (1990) "Afferents to the Cerebellar Nuclei From the Cervical Enlargement in the Rat, as Demonstrated With the Phaseolus Vulgaris Leucoagglutinin Method," *Neurosci. Lett.* 113:253-259.
McLaughlin, S.K. et al. (Jun. 1988). "Adeno-Associated Virus General Transduction Vectors: Analysis of Proviral Structures," *J. Virol.* 62(6):1963-1973.
Miranda, S.R. et al. (Oct. 2000). "Hematopoietic Stem Cell Gene Therapy Leads to Marked Visceral Organ Improvements and a Delayed Onset of Neurological Abnormalities in the Acid Sphingomyelinase Deficient Mouse Model of Niemann-Pick Disease," *Gene Ther.* 7:1768-1776.
Miyazaki, J. et al. (Jul. 15, 1989). "Expression Vector System Based on the Chicken β-Actin Promoter Directs Efficient Production of Interleukin-5," *Gene* 79:269-277.
Muzyczka, N. (1992). "Use of Adeno-Associated Virus as a General Transduction Vector for Mammalian Cells," *Curr. Topics Microb.& Immunol.* 158:97-129.
Neufeld, E.F. et al. (Jul. 10, 1970). "Inborn Errors of Mucopolysaccharide Metabolism. Faulty Degradative Mechanism are Implicated in this Group of Human Diseases," *Science* 169:141-146.
O'Riordan, C.R. et al. (2000, e-pub. Jul. 6, 2000). "Scaleable Chromatographic Purification Process for Recombinant Adeno-Associated Virus (rAAV)," *J. Gene Med.* 2:444-454.

(56) References Cited

OTHER PUBLICATIONS

Otterback, B. et al. (Jun. 30, 1995). "Acid Sphingomyelinase-Deficient Mice Mimic the Neurovisceral Form of Human Lysosomal Storage Disease (Niemann-Pick Disease)," *Cell* 81:1053-1061.

Pardridge, W.M. (1991). *Peptide Drug Delivery to the Brain*, Raven Press, New York, New.York, p. vii, (Table of Contents Only.).

Passini, M.A. et al. (Aug. 1, 2002). "Distribution of a Lysosomal Enzyme in the Adult Brain by Axonal Transport and by Cells of the Rostral Migratory Stream," *J. Neurosci.* 22(15):6437-6446.

Passini, M.A. et al. (2003). "Widespread Gene Delivery and Reversal of Pathology in the Brains of Niemann-Pick a Mice by retrograde Axonal Transport of a Therapeutic AAV Vector," *Meeting for the Society for Neuroscience*, New Orleans, LA, Nov. 8-12, 2003, 1 page. (Abstract Only).

Paxinos, G. (1995). *The Rat Nervous System*, $2^{nd}$ ed., Academic Press. San Diego, California, pp. vii-xii, (Table of Contents Only.).

Rabinowitz, J.E. et al. (Jan. 2002). "Cross-Packaging of a Single Adeno-Associated Virus (AAV) Type 2 Vector Genome Into Multiple AAV Serotypes Enables Transduction with Broad Specificity," *J. Virol.* 76(2):791-801.

Ralph, G.S. et al. (Apr. 2005, e-pub. Mar. 13, 2005). "Silencing Mutant SOD1 Using RNAi Protects Against Neurodegeneration and Extends Survival in an ALS Model," *Nat. Med.* 11(4):429-433.

Raoul, C. et al. (2005). "Lentiviral-Mediated Silencing of SOD1 Through RNA Interference Retards Disease Onset and Progression in a Mouse Model of ALS," *Nat. Med.* 11(4):423-438.

Sambrook, J. et al. (1989). *Molecular cloning: A Laboratory Manual*, $2^{nd}$ Edition, Cold Spring Harbor Laboratory Press, Cold Spring Harbor, New York, pp. v-xxxii, (Table of Contents Only).

Sando, G.N. et al. (Nov. 1977). "Recognition and Receptor-Mediated Uptake of a Lysosomal Enzyme, $\alpha$-L-Iduronidase, by Cultured Human Fibroblasts," *Cell* 12:619-627.

Sarna, J. et al. (2001). "Patterned Cerebellar Purkinje Cell Death in a Transgenic Mouse Model of Niemann Pick Type A/B Disease," *Eur. J. Neurosci.* 13:1873-1880.

Schuchman, E.H. et al. (2001). "Niemann-Pick Disease Types A and B: Acid Sphingomyelinase Deficiencies," Chapter 144 in *The Metabolic and Molecular Bases of Inherited Diseases*, Scriver, C. R. et al, ed., McGraw-Hill, New York, New York, pp. 3589-3610.

Shipley, J.M. et al. (Aug. 1991). "Analysis of the 5' Flanking Region of the Human $\beta$-Glucuronidase Gene," *Genomics* 10:1009-1018.

Skorupa, A.F. et al. (Nov. 1999). "Sustained Production of $\beta$-Glucuronidase from Localized Sites After AAV Vector Gene Transfer Results in Widespread Distribution of Enzyme and Reversal of Lysosomal Storage Lesions in a Large Volume of Brain in Mucopolysaccharidosis VII Mice," *Exp. Neurol.* 160:17-27.

Sleat, D.E. et al. (Oct. 13, 2004). "A Mouse Model of Classical Late-Infantile Neuronal Ceroid Lipofuscinosis Based on Targeted Disruption of the CLN2 Gene Results in a Loss of Tripeptidyl-Peptidase I Activity and Progressive Neurodegeneration," *J. Neurosci.* 24(41):9117-9126.

Slotte, J.P. (1997). "Cholesterol-Sphingomyelin Interactions in Cells—effects on Lipid Metabolism," Chapter 10 in *Subcellular Biochemistry, Cholestrol: Its Functions and Metabolism in Biology and Medicine*, Bittman, R. ed., Plenum Press, New York, New York, 28:277-293.

Soudias, C. et al. (2001, e-pub. Aug. 17, 2001). "Preferential Transduction of Neurons by Canine Adenovirus Vectors and Their Efficient Retrograde Transport in vivo," *FASEB J.* 15:2283-2285, 23 pages.

Stewart, G.R. et al. (2002). Behavioral Pathology of the Niemann-Pick A (ASMKO) Mouse: Structure-Function Studies on Purkinje Cell Degeneration,: *Neuroscience 2002*, Orlando, Florida, Poster 503, Development Disorders: Genetic III Poster, one page. (Abstract Only).

Taylor, R.M. et al. (Jul. 1997). "Decreased Lysosomal Storage in the Adult MPS VII Mouse Brain in the Vicinity of Grafts of Retroviral Vector-Corrected Fibroblasts Secreting High Levels of $\beta$-Glucuronidase," *Nat. Med.* 3(7):771-774.

Tu, P-H. et al. (Apr. 1996). "Transgenic Mice Carrying a Human Mutant Superoxide Dismutase Transgene Develop Neuronla Cytoskeletal Pathology Resembling Human Amyotrophic Lateral Sclerosis Lesions," *Proc. Natl. Acad. Sci. U.S.A.* 93:3155-3160.

Veldwijk, M.R. et I. (Aug. 2002). "Development and Optimization of a Real-Time Quantitative PCR-Based Method for the Titration of AAV-2 Vector Stocks," *Mol. Ther.* 6(2):272-278.

Viana, M.B. et al. (Aug. 1990). "Very Low Levels of High Density Lipoprotein Cholesterol in Four Sibs of a Family with Non-Neuropathic Niemann-Pick Disease and Sea-blue Histiocytosis," *J. Med. Genet.* 27:499-504.

Walkley, S.U. (1998). "Cellular Pathology of Lysosomal Storage Disorders," *Brain Pathol.* 8:175-193.

Watson, D.J. et al. (2003). "Lentiviral Vectors for Gene Transfer to the Central Nervous System. Applications in Lysosomal Storage Disease Animal Models," Chapter 21 in *Methods in Molecular Medicine*,Machida, C.A. ed, Humana Press, Inc., Totowa, New Jersey, 76:383-403.

Xiao, X. et al. (Mar. 1997). "Gene Transfer by Adeno-Associated Virus Vectors Into the Central Nervous System," *Exp. Neurology* 144:113-124.

Xu, R. et al. (Sep. 2001). "Quantitative Comparison of Expression with Adeno-Associated Virus (AAV-2) Brain-specific Gene Cassettes," *Gene Ther.* 8:1323-1332.

Yasojima, K. et al. (Jan. 12, 2001). "Reduced Neprilysin in High Plaque Areas of Alzheimer Brain: A Possible Relationship to Deficient Degradation of $\beta$-Amyloid Peptide," *Neurosci. Lett.* 297:97-100.

Ye, X. et al. (Jan. 1, 1999). "Regulated Delivery of Therapeutic Protiens After in Vivo Somatic Cell Gene Transfer," *Science* 283:88-91.

Yu, J-Y. et al. (Apr. 30, 2002). "RNA Interference by Expression of Short-Interfering RNAs and Hairpin RNAs in Mammalian Cells," *Proc. Natl. Acad. Sci. U.S.A.* 99(9):6047-6052.

Bruijn, L.I. et al. (2004). "Unraveling the Mechanisms Involved in Motor Neuron Degeneration in ALS," *Annu. Rev. Neurosci.* 27:723-749.

Carpenter, S. (Sep. 1968). "Proximal Axonal Enlargement in Motor Neuron Disease," *Neurology* 18:841-851.

Clement, A.M. et al. (Oct. 3, 2003). "Wild-Type Nonneuronal Cells Extend Survival of SOD1 Mutant Motor Neurons in ALS Mice," *Science* 302:113-117, erratum Oct. 24, 2003, 1 page.

Cleveland, D.W. et al. (Nov. 2001). "From Charcot to Lou Gehrig: Deciphering Selective Motor Neuron Death in ALS," *Nat. Rev. Neurosci.* 2(11):806-819.

Delisle, M.B. et al. (Feb. 1984). Neurofibrillary Axonal Swellings and Amyotrophic Lateral Sclerosis. *J. Neurol. Sci.* 63(2):241-250.

Doré, S. et al. (Aug. 1997). "Rediscovering an Old Friend, IGF-I: Potential Use in the Treatment of Neurodegenerative Diseases," *Trends Neurosci.* 20(8):326-331.

Gurney, M.E. et al. (Jun. 17, 1994). "Motor Neuron Degeneration in Mice That Express a Human Cu,Zn Superoxide Dismutase Mutation," *Science* 264:1772-1775.

Hirano, A. et al. (Sep. 1984). "Fine Structural Study of Neurofibrillary Changes in a Family With Amyotrophic Lateral Sclerosis," *J. Neuropathol. & Exp. Neurol.* 43(5):471-480.

Hirano, A. (Oct. 1996). "Neuropathology of ALS: An Overview," *Neurology* 47(Supp. 2):S63-S66.

Leigh, P.N. et al. (1991). "Cytoskeletal Pathology in Motor Neuron Diseases," *Adv. Neurol.* 56:115-124.

Leigh, P.N. et al. (Apr. 1991). "Ubiquitin-Immunoreactive Intraneuronal Inclusions in Amyotrophic Lateral Sclerosis. Morphology, Distribution, and Specificity," *Brain* 114( Pt 2):775-788.

Matsushita, M. et al. (Sep. 29, 1987). "Projections From the Thoracic Cord to the Cerebellar Nuclei in the Rat, Studied by Anterograde Axonal Tracing," *J. Comp. Neurol.* 386(3):409-421.

Matsushita, M. et al. (Mar. 1995). "Projections From the Central Cervical Nucleus to the Cerebellar Nuclei in the Rat, Studied by Anterograde Axonal Tracing," *J. Comp. Neurol.* 353:(2)234-246.

Matsushita, M. et al. (Jan. 13, 1997). "Projections From the Cervical Enlargement to Cerebellar Nuclei in the Rat, Studied by Anterograde Axonal Tracing," *J. Comp. Neurol.* 377:251-261.

(56) References Cited

OTHER PUBLICATIONS

Matsushita, M. (Feb. 1, 1999). "Projections From the Lowest Lumbar and Sacral-Caudal Segments to the Cerebellar Nuclei in the Rat, Studied by Anterograde Axonal Tracing," *J. Comp. Neurol.* 404(1):21-32.

Rosen, D.R. et al. (Mar. 4, 1993). "Mutations in Cu/Zn Superoxide Dismutase Gene are Associated With Familial Amyotrophic Lateral Sclerosis," *Nature* 362(6415):59-62.

Rowland, L.P. et al. (May 31, 2001). Amyotrophic Lateral Sclerosis. *N. Engl. J. Med.* 344(22):1688-1700.

Duvernoy, H.M. (1999). *The Human Brain. Surface, Three-Dimensional Sectional Anatomy.With MRI, and Blood Supply*, SpringerWien, New York, New York, five pages, (Table of Contents).

Talairach et al. (1988). *Co-Planar Stereotaxic Atlas of the Human Brain: 3-Dimensional.Proportional System: An Approach to Cerebral Imaging*, (Table of Contents.), 2 pages.

Wu, Z. et al. (Sep. 2006). "α2,3 and α2,6 N-linked sialic acids facilitate efficient binding and transduction by adeno-associated virus types 1 and 6," *Journal of Virology* 80(18):9093-9103.

International Search Report, dated Sep. 15, 2006, for PCT Application No. PCT/US06/17242, filed on May 2, 2006, two pages.

The Extended European Search Report dated Jan. 23, 2012, for European Patent Application No. 11169633.2, filed on May 2, 2006, five pages.

Hauck, B. et al. (Feb. 2003). "Characterization of Tissue Tropism Determinants of Adeno-Associated Virus Type 1", *Journal of Virology* 77(4):2768-2774.

Ding, W. et al. (2005, e-pub. Apr. 14, 2005). "Intracellular Trafficking of Adeno-Associated Viral Vectors," *Gene Therapy* 12:873-880.

Prell, T. et al. (Dec. 2013, e-pub. Jul. 29, 2013). "The Involvement of the Cerebellum in Amyotrophic Lateral Sclerosis," *Amyotroph Lateral Scler Frontotemporal Degener* 14(7-8):507-515, 9 pages.

Vite, C.H. et al. (2003). "Adeno-Associated Virus Vector-Mediated Transduction in the Cat Brain," *Gene Therapy* 10:1874-1881.

Wang, C. et al. (2003). "Recombinant AAV Serotype 1 Transduction Efficiency and Tropism in the Murine Brain," *Gene Therapy* 10:1528-1534.

Lebherz, C. et al. (Jun. 2004, e-pub. Mar. 2, 2004). "Gene Therapy with Novel Adeno-Associated Virus Vectors Substantially Diminishes Atherosclerosis in a Murine Model of Familial Hypercholesterolemia," J Gene Med. 6(6):663-672.

\* cited by examiner

SEQUENCE LISTING

<160> NUMBER OF SEQ ID NOS: 2

<210> SEQ ID NO 1
<211> LENGTH: 153
<212> TYPE: PRT
<213> ORGANISM: Homo sapiens

<400> SEQUENCE: 1

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

<210> SEQ ID NO 2
<211> LENGTH: 195
<212> TYPE: PRT
<213> ORGANISM: Homo sapiens

<400> SEQUENCE: 2

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45
```

```
Gly Pro Glu Thr Leu Cys Gly Ala Glu Leu Val Asp Ala Leu Gln Phe
    50              55              60

Val Cys Gly Asp Arg Gly Phe Tyr Phe Asn Lys Pro Thr Gly Tyr Gly
65              70              75              80

Ser Ser Ser Arg Arg Ala Pro Gln Thr Gly Ile Val Asp Glu Cys Cys
            85              90              95

Phe Arg Ser Cys Asp Leu Arg Arg Leu Glu Met Tyr Cys Ala Pro Leu
            100             105             110

Lys Pro Ala Lys Ser Ala Arg Ser Val Arg Ala Gln Arg His Thr Asp
        115             120             125

Met Pro Lys Thr Gln Lys Tyr Gln Pro Pro Ser Thr Asn Lys Asn Thr
    130             135             140

Lys Ser Gln Arg Arg Lys Gly Trp Pro Lys Thr His Pro Gly Gly Glu
145             150             155             160

Gln Lys Glu Gly Thr Glu Ala Ser Leu Gln Ile Arg Gly Lys Lys Lys
            165             170             175

Glu Gln Arg Arg Glu Ile Gly Ser Arg Asn Ala Glu Cys Arg Gly Lys
            180             185             190

Lys Gly Lys
        195
```

GENE THERAPY FOR SPINAL CORD DISORDERS

This application claims priority under 35 U.S.C. § 119(e) to U.S. Provisional Application No. 60/677,213, filed May 2, 2005, and U.S. Provisional Application No. 60/790,217, filed Apr. 8, 2006, the contents of which are herein incorporated by reference.

FIELD OF THE INVENTION

The present invention relates to compositions and methods for treating disorders affecting a subject's motor function and in particular, motor function affected by disease or injury to the brain and/or spinal cord.

BACKGROUND OF THE INVENTION

Gene therapy is an emerging treatment modality for disorders affecting the central nervous system (CNS). CNS gene therapy has been facilitated by the development of viral vectors capable of effectively infecting post-mitotic neurons. The central nervous system is made up of the spinal cord and the brain. The spinal cord conducts sensory information from the peripheral nervous system to the brain and conducts motor information from the brain to various effectors. For a review of viral vectors for gene delivery to the central nervous system, see Davidson et al. (2003) Nature Rev. 4:353-364.

Adeno-associated virus (AAV) vectors are considered useful for CNS gene therapy because they have a favorable toxicity and immunogenicity profile, are able to transduce neuronal cells, and are able to mediate long-term expression in the CNS (Kaplitt et al. (1994) Nat. Genet. 8:148-154; Bartlett et al. (1998) Hum. Gene Ther. 9:1181-1186; and Passini et al. (2002) J. Neurosci. 22:6437-6446).

One useful property of AAV vectors lies in the ability of some AAV vectors to undergo retrograde and/or anterograde transport in neuronal cells. Neurons in one brain region are interconnected by axons to distal brain regions thereby providing a transport system for vector delivery. For example, an AAV vector may be administered at or near the axon terminals of neurons. The neurons internalize the AAV vector and transport it in a retrograde manner along the axon to the cell body. Similar properties of adenovirus, HSV, and pseudo-rabies virus have been shown to deliver genes to distal structures within the brain (Soudas et al. (2001) FASEB J. 15:2283-2285; Breakefield et al. (1991) New Biol. 3:203-218; and deFalco et al. (2001) Science, 291:2608-2613).

Several groups have reported that the transduction of the brain by AAV serotype 2 (AAV2) is limited to the intracranial injection site (Kaplitt et al. (1994) Nat. Genet. 8:148-154; Passini et al. (2002) J. Neurosci. 22:6437-6446; and Chamberlin et al. (1998) Brain Res. 793:169-175). Recent reports suggest that retrograde axonal transport of neurotropic viral vectors can also occur in select circuits of the normal rat brain (Kaspar et al. (2002) Mol. Ther. 5:50-56 (AAV vector); Kasper et al. (2003) Science 301:839-842 (lentiviral vector) and Azzouz et al. (2004) Nature 429:413-417 (lentiviral vector). Roaul et al. (2005) Nat. Med. 11(4): 423-428 and Ralph et al. (2005) Nat. Med. 11(4):429-433 report that intramuscular injection of lentivirus expressing silencing human Cu/Zn supreoxide dismutase (SOD1) interfering RNA retarded disease onset of amyotrophic lateral sclerosis (ALS) in a therapeutically relevant rodent model of ALS.

Cells transduced by AAV vectors may express a therapeutic transgene product, such as an enzyme or a neurotrophic factor, to mediate beneficial effects intracellularly. These cells may also secrete the therapeutic transgene product, which may be subsequently taken up by distal cells where it may mediate its beneficial effects. This process has been described as cross-correction (Neufeld et al. (1970) Science 169:141-146).

However, a need still exists for compositions and methods to treat dysfunction of the spinal cord that result in loss of motor function in human patients. This invention satisfies this need and provides related advantages as well.

SUMMARY OF THE INVENTION

This invention provides methods and compositions to deliver a transgene to the spinal cord and/or the brainstem region of a subject by administering a recombinant neurotropic viral vector containing the transgene to at least one region of the deep cerebellar nuclei (DCN) region of the subject's brain. The viral delivery is under conditions that favor expression of the transgene in the spinal cord and/or the brainstem region.

In another aspect, the invention provides methods and compositions to deliver a transgene to a subject's spinal cord by administering a recombinant neurotropic viral vector containing the transgene to the motor cortex region of the subject's brain. The delivery of the viral vector is under conditions that favor expression of the transgene in the spinal cord. Viral vectors administered to the motor cortex region are internalized by motor neurons via their cell body region and the transgene is expressed. The expressed transgene may then undergo anterograde transport to the axon terminal portion of the motor neuron, which is present in the spinal cord. Due to the nature of the motor cortex, viral vectors administered to this region of the brain may also be internalized by axon terminals of motor neurons. The viral vector also may undergo retrograde transport along the motor neuron's axon and be expressed in the cell body of the motor neuron.

Further provided are compositions and methods to deliver a transgene to a motor neuron in a subject by administering a recombinant neurotropic viral vector containing the transgene to at least one region of the deep cerebellar nuclei region of the subject's brain. The delivery of the vector is under conditions that favor expression of the transgene in a motor neuron distal to the site of administration.

Also provided are methods and compositions to deliver a transgene to a motor neuron in a subject by administering a neurotropic viral vector containing the transgene to the motor cortex region of the subject's brain and wherein the administration is under conditions that favor expression of the transgene in a motor neuron distal to the site of administration.

In an alternate aspect, the invention provides compositions and methods to treat a motor neuron disorder in a subject by administering a recombinant neurotropic viral vector containing a therapeutic transgene to at least one region of the deep cerebellar nuclei region of the subject's brain. Administration is done under conditions that favor expression of a therapeutically effective amount of the transgene in at least one subdivision of the spinal cord and/or the brainstem region.

In yet a further aspect, the invention provides compositions and method to ameliorate the symptoms of a motor neuron disorder in a subject by administering a recombinant neurotropic viral vector containing the therapeutic transgene to the motor cortex region of the subject's brain and under conditions that favor expression of the transgene in a therapeutically effective amount in at least one subdivision of the spinal cord and/or the brainstem region.

It is to be understood that both the foregoing general description and the following detailed description are exemplary and explanatory only and are not restrictive of the invention as claimed.

BRIEF DESCRIPTION OF THE FIGURES

FIGS. 2 through 5 are reproduced from Williams et al. (2005) The Human Brain Chapter 3: The Cerebellum, available at the web site: www.vh.org/adult/provider/anatomy/BrainAnatomy/Ch3Text/Section07.html.

DETAILED DESCRIPTION OF THE INVENTION

Figure 1:
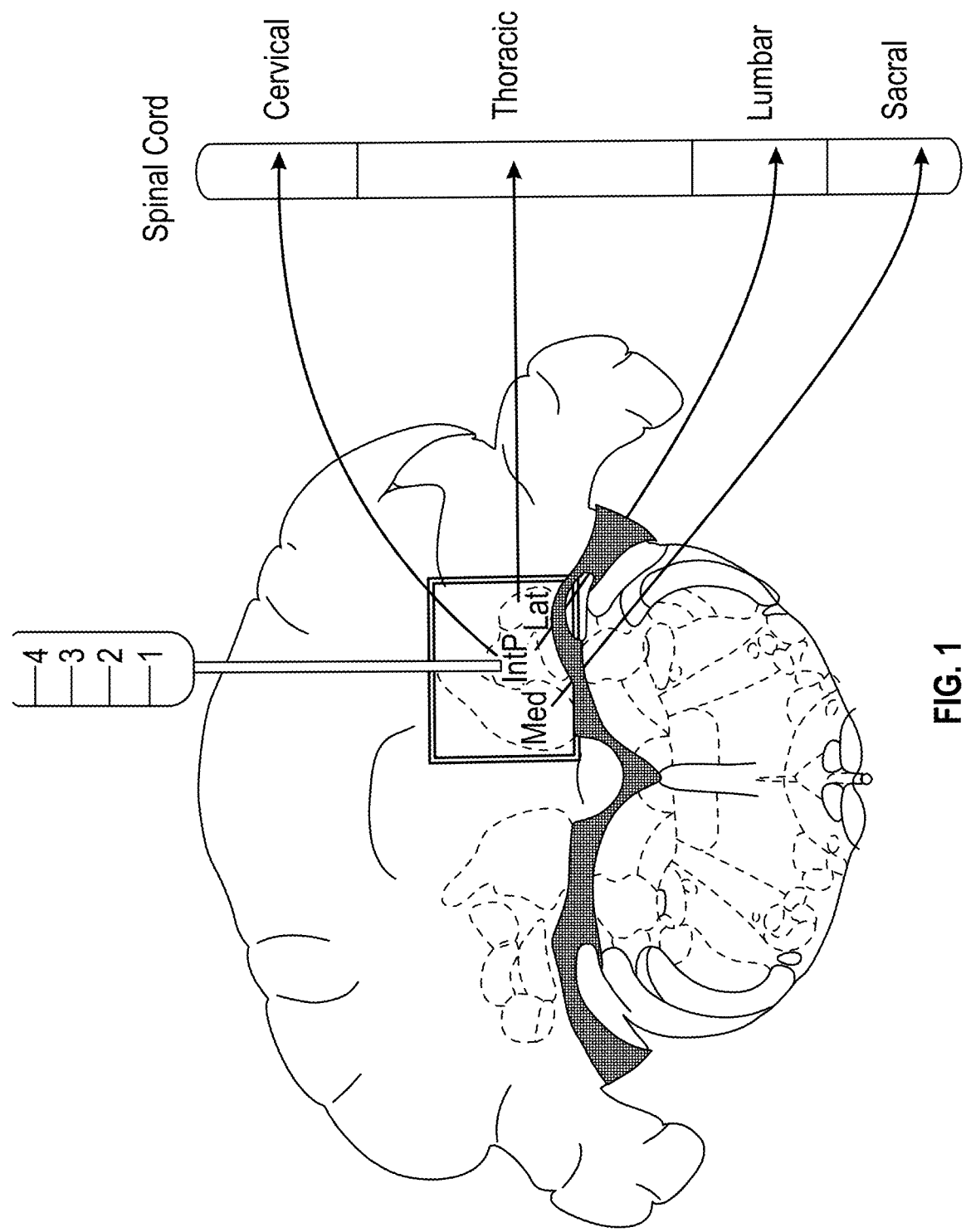
FIG. 1 is a schematic of how the DCN could be used to transport therapeutic virus to the spinal cord. Lines originating within the black box outlining the DCN represent axons terminals originating from cell bodies (arrowheads) localized within the spinal cord.

In order that the present invention may be more readily understood, certain terms are first defined. Additional definitions are set forth throughout the detailed description.

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, 2$^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The term "transgene" refers to a polynucleotide that is introduced into a cell of and is capable of being transcribed into RNA and optionally, translated and/or expressed under appropriate conditions. It one aspect, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," or "genome equivalents," as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

The terms "therapeutic," "therapeutically effective amount," and their cognates refer to that amount of an RNA, DNA or expression product of DNA and/or RNA that results in prevention or delay of onset or amelioration of symptoms of in a subject or an attainment of a desired biological outcome, such as correction of neuropathology, e.g., cellular pathology associated with a motor neuronal disease such as ALS. The term "therapeutic correction" refers to that degree of correction that results in prevention or delay of onset or amelioration of symptoms in a subject. The effective amount can be determined by known empirical methods.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provision that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

A "subject," "individual" or "patient" is used interchangeably herein, which refers to a vertebrate, preferably a mammal, more preferably a human. Mammals include, but are not limited to, murines, rats, simians, humans, farm animals, sport animals, and pets.

A "control" is an alternative subject or sample used in an experiment for comparison purpose. A control can be "positive" or "negative". For example, where the purpose of the experiment is to determine a correlation of an altered expression level of a gene with a particular type of pathology (see ALS, for example, infra), it is generally preferable to use a positive control (a subject or a sample from a subject, carrying such alteration and exhibiting symptoms characteristic of that disease), and a negative control (a subject or a sample from a subject lacking the altered expression and clinical symptom of that disease).

"Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to a differential that is at least 1.5 times, or at least 2.5 times, or alternatively at least 5 times, or alternatively at least 10 times higher or lower than the expression level detected in a control sample. The term "differentially expressed" also refers to nucleotide sequences in a cell or tissue which are expressed where silent in a control cell or not expressed where expressed in a control cell.

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example one may ameliorate the symptoms of a disease or disorder by making them more bearable.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads are easy to grow and do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

The invention provides a method to deliver a transgene to the spinal cord and/or brainstem in a subject by administering a recombinant neurotropic viral vector containing a transgene to at least one region of the deep cerebellar nuclei region of the brain, wherein the delivery is under conditions that favor expression of the transgene at a site distal to the site of administration. The delivery may also result in expression of the transgene at the site of administration.

Unless specifically indicated to the contrary, expression of the transgene is not limited to translation to a polypeptide or protein but also includes replication and/or transcription of the transgene polynucleotide.

In another aspect, the invention provides a method of delivering a therapeutic transgene product to a target cell of the CNS, which is a neuron or a glial cell, in a mammal afflicted with a motor neuronal disorder, e.g., ALS or traumatic spinal cord injury. The transgene may encode for IGF-1.

In another aspect, the invention is a method to deliver a transgene to the spinal cord in a subject by administering a recombinant neurotropic viral vector containing said transgene to the motor cortex region of the brain, wherein said delivery is under conditions that favor expression of said transgene at a site distal to said site of administration.

In a yet further aspect, the invention the viral vector is administered to at least one region of the deep cerebellar nuclei region of the brain where the transgene product is expressed and delivered to the spinal cord and/or the brainstem region of the subject.

In another embodiment, the viral vector is administered to at least one region of the deep cerebellar nuclei region of the brain that is interconnected with brainstem and spinal motor neurons. These targeted regions have direct connections with cells (e.g., interneurons and astrocytes) that compose the motor neuron's cellular environment. The administration delivers the transgene product to the motor neuron's cellular environment, where the product mediates a beneficial effect on the cells that compose it.

In one embodiment, the invention is a method to deliver a transgene to or modulate its expression, in a motor neuron in a subject by administering a neurotropic viral vector containing the transgene to the motor cortex region of the brain of the subject, wherein the transgene is expressed in a region of the motor neuron distal to said site of administration.

In an alternate embodiment, the invention is a method to treat a motor neuron disorder in a subject by administering a recombinant neurotropic viral vector containing a therapeutic transgene to at least one region of the deep cerebellar nuclei region of the brain of the subject, wherein the transgene is expressed in a therapeutically effective amount in at least one subdivision of the spinal cord of the subject. These subdivisions include one or more of cervical, thoracic, lumbar or sacral (see FIG. 1, FIG. 12A). The transgene may also be expressed in a therapeutically effective amount in at least one region of the brainstem, such as, for example, the midbrain, pons, or medulla (see FIG. 12B). It may also be expressed in a therapeutically effective amount in both at least one region of the brainstem and in at least one subdivision of the spinal cord of the subject.

This invention also is a method to ameliorate the symptoms of a motor neuron disorder in a subject by administering a recombinant neurotropic viral vector containing a therapeutic transgene to the motor cortex region of the brain, wherein said transgene is expressed in a therapeutically effective amount in at least one subdivision of the spinal cord of the subject. These subdivisions include one or more of cervical, thoracic, lumbar or sacral (see FIG. 1, FIG. 12A).

Suitable neurotropic viral vectors for the practice of this invention include, but are not limited to adeno-associated viral vectors (AAV), herpes simplex viral vectors (U.S. Pat. No. 5,672,344) and lentiviral vectors.

In the methods of the invention, AAV of any serotype can be used. In certain embodiments, AAV of any serotype can be used so long as the vector is capable of undergoing retrograde axonal transport in a disease-compromised brain, or axonal transport in a non-compromised brain. The serotype of the viral vector used in certain embodiments of the invention is selected from the group consisting from AAV1, AAV2, AAV3, AAV4, MV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Aurichio et al., (2001) Hum. Mol. Genet., 10(26):3075-81).

AAV vectors are derived from single-stranded (ss) DNA parvoviruses that are nonpathogenic for mammals (reviewed in Muzyscka (1992) Curr. Top. Microb. Immunol., 158:97-129). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV2 or AAV1. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888. Additional exemplary AAV vectors are recombinant AAV2/1, AAV2/2, AAV2/5, AAV2/7 and AAV2/8 serotype vectors encoding human protein.

In certain methods of the invention, the vector comprises a transgene operably linked to a promoter. The transgene encodes a biologically active molecule, expression of which in the CNS results in at least partial correction of neuropathology. The genomic and functional cDNA sequences of human ASM have been published (see, e.g., U.S. Pat. Nos. 5,773,278 and 6,541,218). The Insulin-like growth factor (IGF-1) gene has a complex structure, which is well-known in the art. It has at least two alternatively spliced mRNA products arising from the gene transcript. There is a 153 amino acid peptide, known by several names including IGF-1A or IGF-1Ea, and a 195 amino acid peptide, known by several names including IGF-1B or IGF-1Eb. The mature form of IGF-1 is a 70 amino acid polypeptide. Both IGF-1 Ea and IGF-1 Eb contain the 70 amino acid mature peptide, but differ in the sequence and length of their carboxyl-terminal extensions. The peptide sequences of IGF-1 Ea and IGF-1 Eb are represented by SEQ ID NOS: 1 and 2, respectively. The genomic and functional cDNAs of human IGF-1, as well as additional information regarding the IGF-1 gene and its products, are available at Unigene Accession No. NM_00618.

The level of transgene expression in eukaryotic cells is largely determined by the transcriptional promoter within the transgene expression cassette. Promoters that show long-term activity and are tissue- and even cell-specific are used in some embodiments. Nonlimiting examples of promoters include, but are not limited to, the cytomegalovirus (CMV) promoter (Kaplitt et al. (1994) Nat. Genet. 8:148-154), CMV/human β3-globin promoter (Mandel et al. (1998) J. Neurosci. 18:4271-4284), GFAP promoter (Xu et al. (2001) Gene Ther. 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277), the β-glucuronidase (GUSB) promoter (Shipley et al. (1991) Genetics 10:1009-1018), and ubiquitin promoters such as those isolated from human ubiquitin A, human ubiquitin B, and human ubiquitin C as described in U.S. Pat. No. 6,667,174. To prolong expression, other regulatory elements may additionally be operably linked to the transgene, such as, e.g., the Woodchuck Hepatitis Virus Post-Regulatory Element (WPRE) (Donello et al. (1998) J. Virol. 72:5085-5092) or the bovine growth hormone (BGH) polyadenylation site.

For some CNS gene therapy applications, it may be necessary to control transcriptional activity. To this end, pharmacological regulation of gene expression with viral vectors can been obtained by including various regulatory elements and drug-responsive promoters as described, for example, in Haberma et al. (1998) Gene Ther. 5:1604-16011; and Ye et al. (1995) Science 283:88-91.

In the methods of this invention, the viral vector can be administered by contacting an terminal axonal ending of a neuron with a composition containing a viral vector carrying the transgene, allowing the viral particle to be endocytosed and transported intracellularly (retrogradely) along the axon to the cell body of the neuron; allowing the therapeutic transgene product to be expressed, wherein the therapeutic transgene product thereby alleviates pathology in the subject. The effect may be on motor neurons, on cells that compose the motor neuron environment (such as interneurons and astrocytes), or on both. In certain embodiments, the concentration of the vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml).

In additional methods of this invention, the viral vector can be administered by contacting the cell body of a neuron with a composition containing a viral vector carrying the transgene, allowing the viral particle to be endocytosed, allowing the therapeutic transgene product to be expressed and transported anterogradely intracellularly along the axon to the axon terminal of the neuron, wherein the therapeutic transgene product thereby alleviates pathology in the subject. The effect may be on motor neurons, on cells that compose the motor neuron environment (such as interneurons and astrocytes), or on both. In certain embodiments, the concentration of the vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml).

In one aspect, the transgene encodes a biologically active molecule, expression of which in the CNS results in at least partial correction of neuropathology. In some embodiments, the therapeutic transgene product is an RNA molecule that inhibits expression of SOD in a subject thereby alleviating and preventing the symptoms of ALS. See Roaul et al. (2005) Nat. Med. 11(4):423-428 and Ralph et al. (2005) Nat. Med. 11(4):429-433.

In one aspect when performing these methods, the transgene expresses a therapeutic amount of a protein selected from the group consisting of insulin growth factor-1 (IGF-1), calbindin D28, parvalbumin, HIF1-alpha, SIRT-2, VEGF, EPO (erythropoietin), CBP (cAMP response element binding protein [CREB] binding protein), SMN-1, SMN-2, and CNTF (Ciliary neurotrophic factor).

Alternatively, the transgene inhibits expression of a mutant form of a protein, e.g., mutant SOD that results in ALS. Roaul et al. (2005) supra and Ralph et al. (2005) supra.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Sterotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000. FIG. 1 schematically shows the spinal cord and its four subdivisions: cervical, thoracic, lumbar and sacral.

The subject invention provides methods to modulate, correct or augment motor function in a subject afflicted with motor neuronal damage. For the purpose of illustration only, the subject may suffer from one or more of amytrophic lateral sclerosis (ALS), spinal bulbar muscular atrophy, spinal muscular atrophy, spinal cerebellar ataxia, primary lateral sclerosis (PLS), or traumatic spinal cord injury.

Without being limited as to theory, the pathology associated with motor neuron damage may include motor neuron degeneration, gliosis, neurofilament abnormalities, loss of myelinated fibers in corticospinal tracts and ventral roots. For example, two types of onset have been recognized: bulbar onset, which affects the upper motor neurons (cortex and brainstem motor neurons), affects the facial muscles, speech, and swallowing; and limb onset, which affects the lower motor neurons (spinal cord motor neurons), is reflected by spasticity, generalized weakness, muscular atrophy, paralysis, and respiratory failure. In ALS, subjects have both bulbar and limb onset. In PLS, subjects have bulbar onset.

Figure 12A:
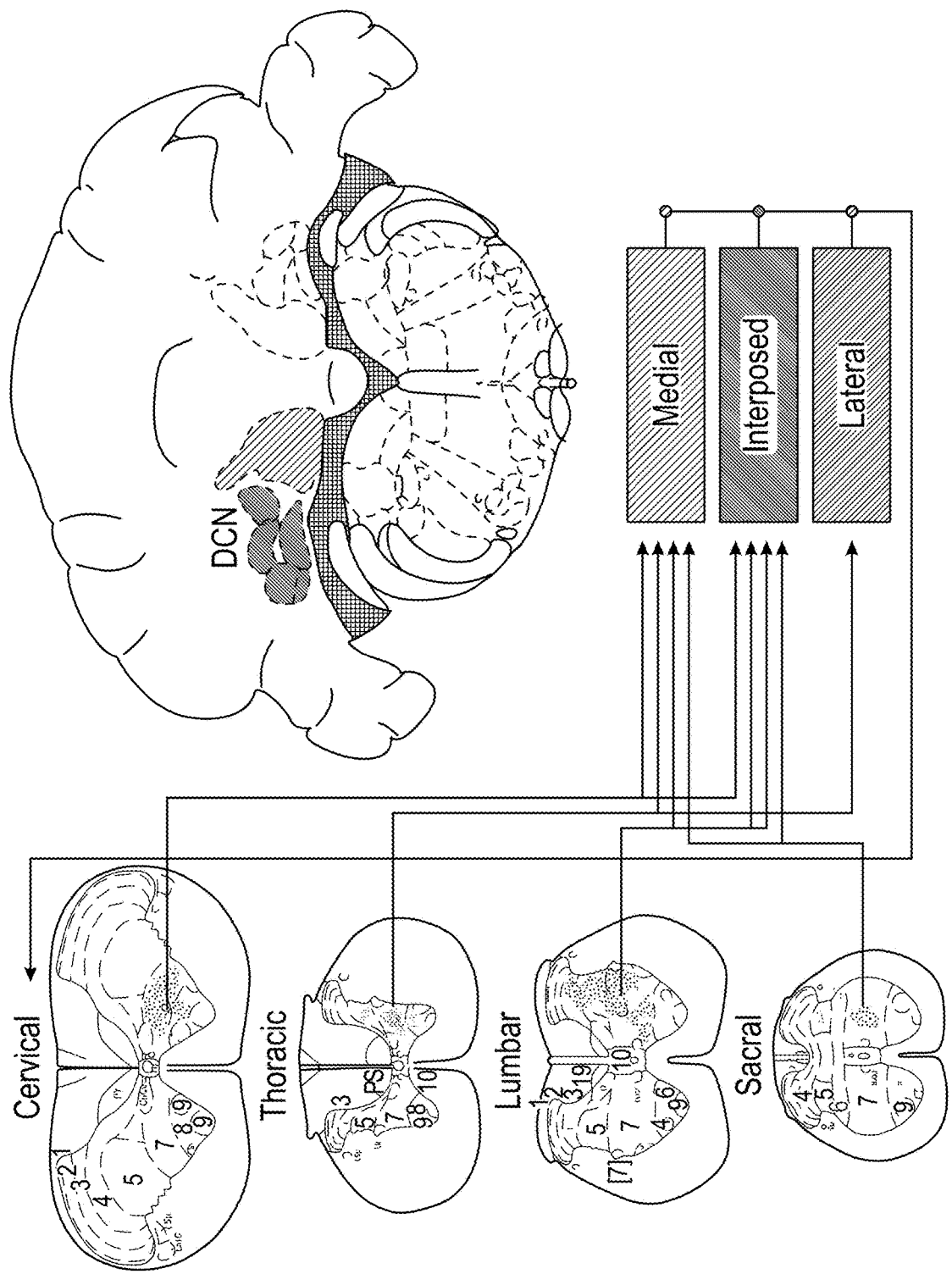
FIG. 12A illustrates the connections between the deep cerebellar nuclei regions (medial, interposed, and lateral) and the spinal cord regions (cervical, thoracic, lumbar, and sacral).
Figure 12B:
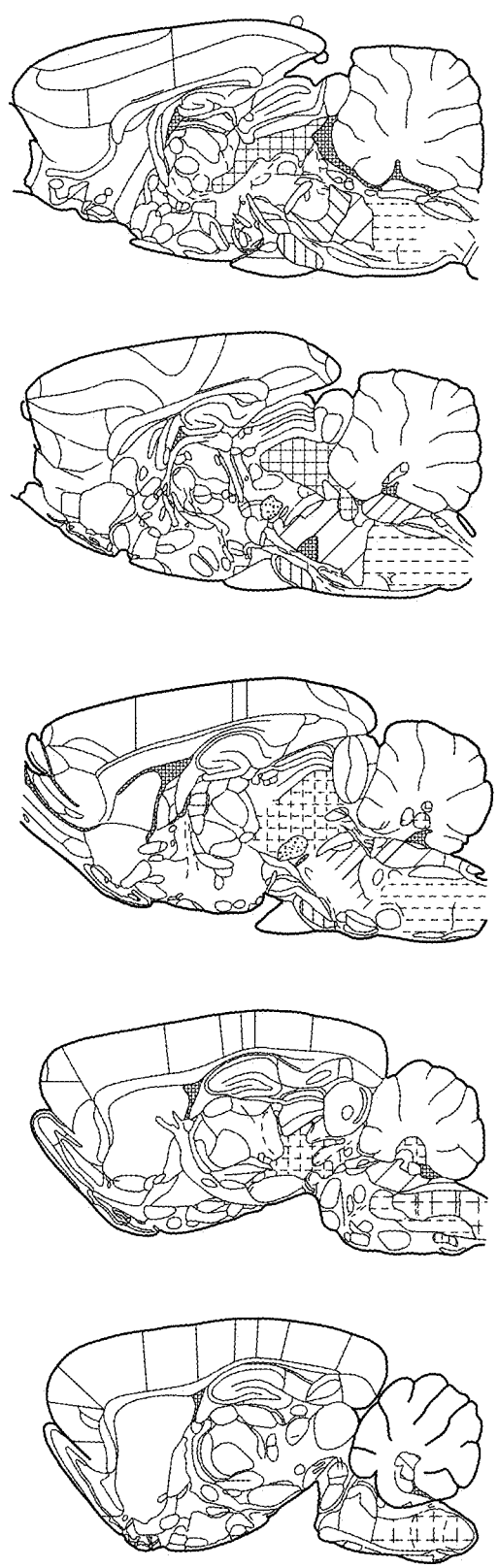
FIG. 12B illustrates the connections between the deep cerebellar nuclei regions (medial, interposed, and lateral) and the brainstem regions (midbrain, pons, and medulla). The connections are represented by arrows, which start at the cell body region of a neuron and end at the axon terminal region of the neuron. For example, the three regions of the DCN each have neurons with cell bodies that send axons that terminate in the cervical region of the spinal cord while the cervical region of the spinal cord has cell bodies that send axons that terminate in either the medial or interposed regions of the DCN.
Figure 12B:
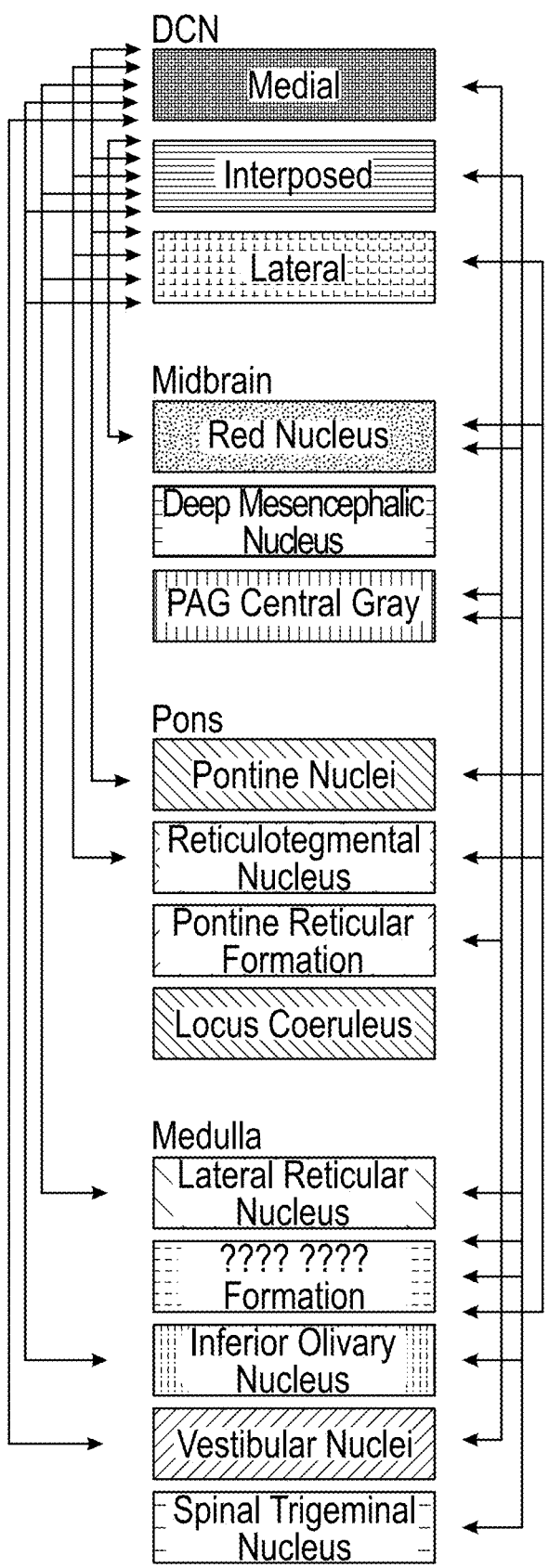

Without being limited as to theory, one embodiment of the invention lies in the ability to provide a therapeutic molecule (for example, a protein or peptide) to each division of the spinal cord. This may be accomplished by injecting an AAV vector into the DCN. Furthermore, it may be important to target individual lamina within each spinal cord division. Lamina are specific sub-regions within regions of the brain and spinal cord. It may be desirable in certain embodiments to target specific lamina within a certain spinal cord division. Since motor neuron damage may occur within the upper motor neurons as well, it may also be desirable to provide a therapeutic molecule (for example, a protein or peptide) to the divisions of the brainstem. In one embodiment, it may be desirable to provide the therapeutic molecule to both the spinal cord, including some or all subdivisions as well as to the brainstem, including some or all subdivisions. The instant invention uses the introduction of an AAV vector into the DCN to accomplish the above described delivery of a therapeutic molecule to the spinal cord region(s) and/or brainstem. FIG. 12A illustrates the connections between the deep cerebellar nuclei regions and the spinal cord while FIG. 12B illustrates the connections between the deep cerebellar nuclei regions and the brainstem.

The ability to organize and execute complex motor acts depends on signals from the motor areas in the cerebral cortex, i.e., the motor cortex. Cortical motor commands descend in two tracts. The corticobular fibers control the motor nuclei in the brain stem that move facial muscles and the corticospinal fibers control the spinal motor neurons that innervate the trunk and limb muscles. The cerebral cortex also indirectly influences spinal motor activity by acting on the descending brain stem pathways.

The primary motor cortex lies along the precentral gyrus in Broadmann's area (4). The axons of the cortical neurons that project to the spinal cord run together in the corticospinal tract, a massive bundle of fibers containing about 1 million axons. About a third of these originate from the precentral gyrus of the frontal lobe. Another third originate from area 6. The remainder originates in areas 3, 2, and 1 in the somatic sensory cortex and regulate transmission of afferent input through the dorsal horn.

The corticospinal fibers run together with corticobulbar fibers through the posterior limb of the internal capsule to reach the ventral portion of the midbrain. They separate in the pons into small bundles of fibers that course between the pontine nuclei. They regroup in the medulla to form the medullary pyramid. About three-quarters of the corticospinal fibers cross the midline in the pyramidal decussation at the junction of the medulla and spinal cord. The crossed fibers descend in the dorsal part of the lateral columns (dorsolateral column) of the spinal cord, forming the lateral corticospinal tract. The uncrossed fibers descend in the ventral columns as the ventral corticospinal tract.

Figure 3:
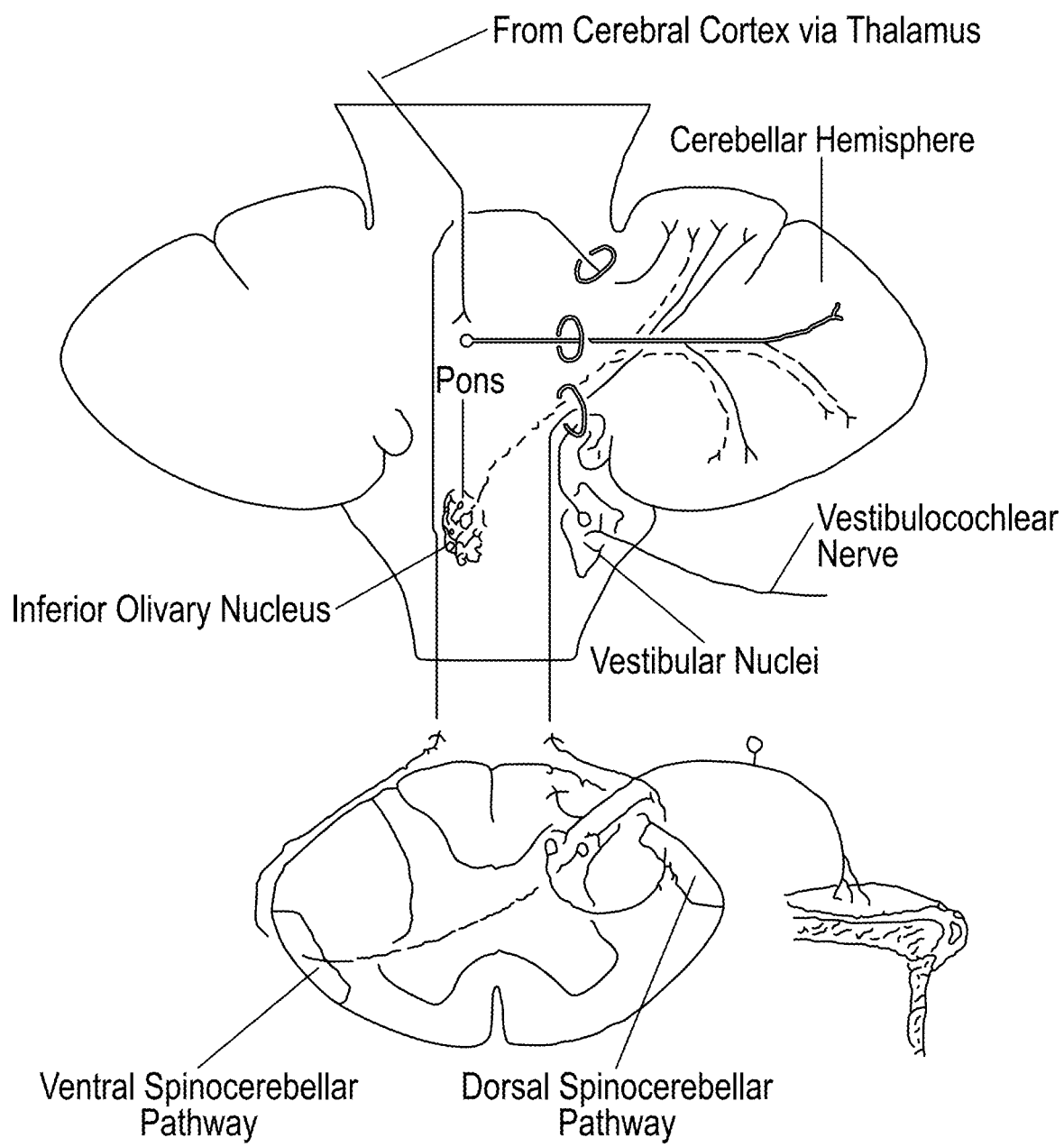
FIG. 3 is a schematic view of the cerebellum which has been cut along the line of the vermis (sagittal section) and then flattened, as well as a horizontal section through the spinal cord and a representation of skeletal musculature. It shows the major afferent (input) pathways.

The lateral and ventral divisions of the corticospinal tract terminate in about the same regions of spinal gray matter as the lateral and medial systems of the brain stem. The lateral corticospinal tract projects primarily to motor nuclei in the lateral part of the ventral horn and to interneurons in the intermediate zone. The ventral corticospinal tract projects bilaterally to the ventromedial cell column and to adjoining portions of the intermediate zone that contain the motor neuorons that innervate axial muscles. FIG. 3 schematically shows the major afferent (input) pathways.

Figure 2:
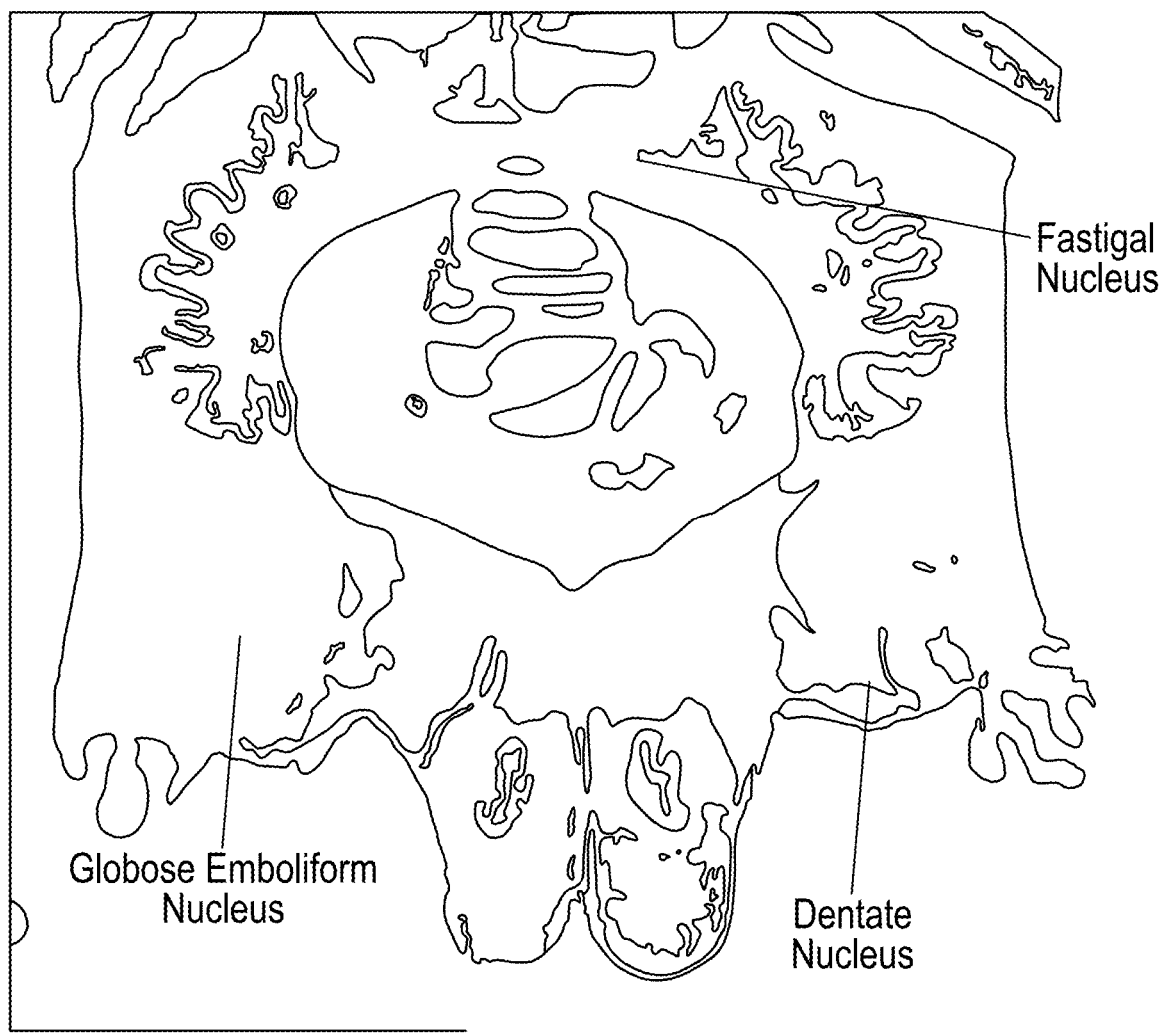
FIG. 2 is a reproduction of a histological transverse section through the ponto-medullary junction and cerebellum, showing the three regions of the DCN.
Figure 4:
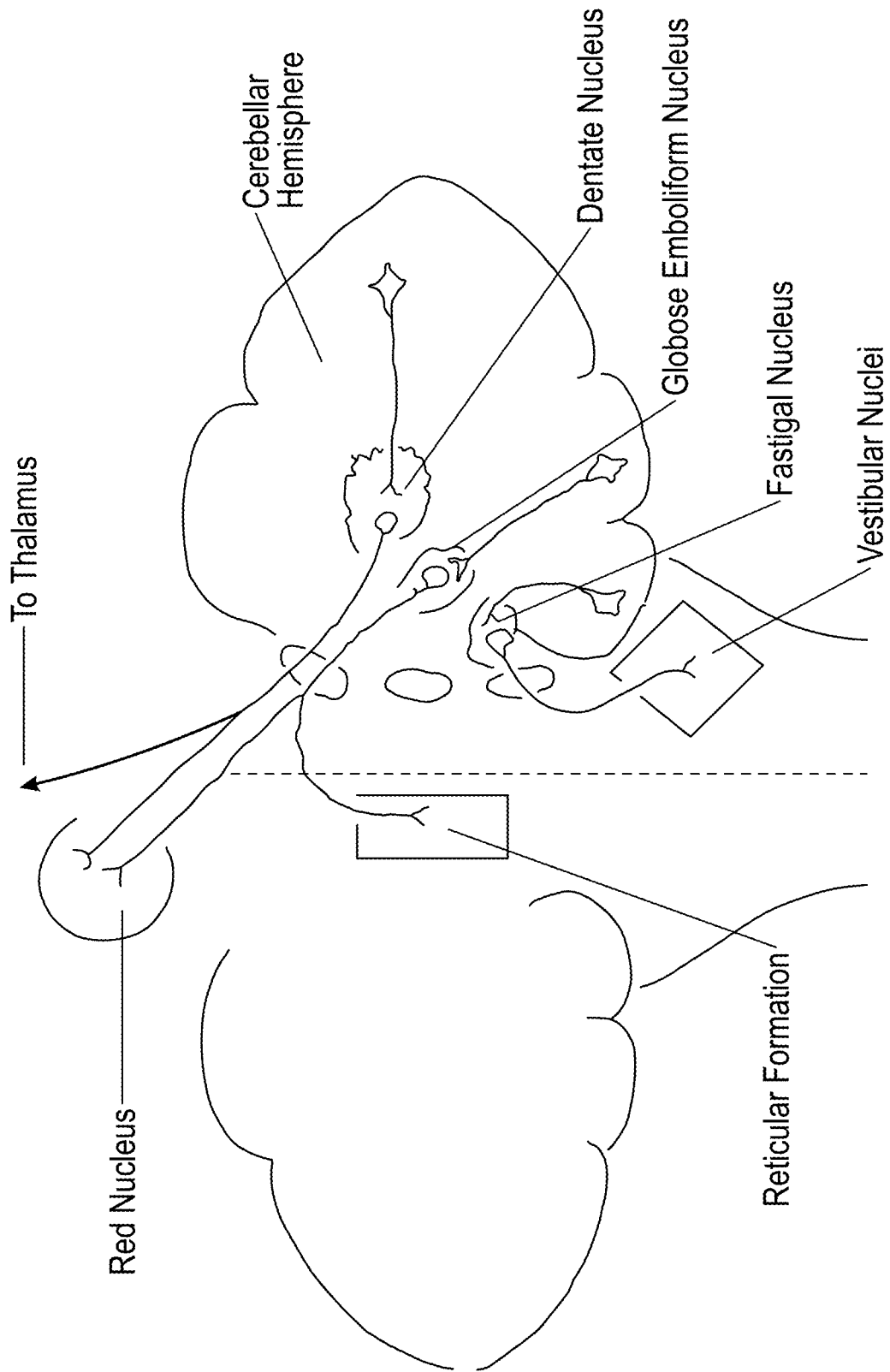
FIG. 4 is a diagram showing the major efferent pathways (outputs) of the DCN.
Figure 5:
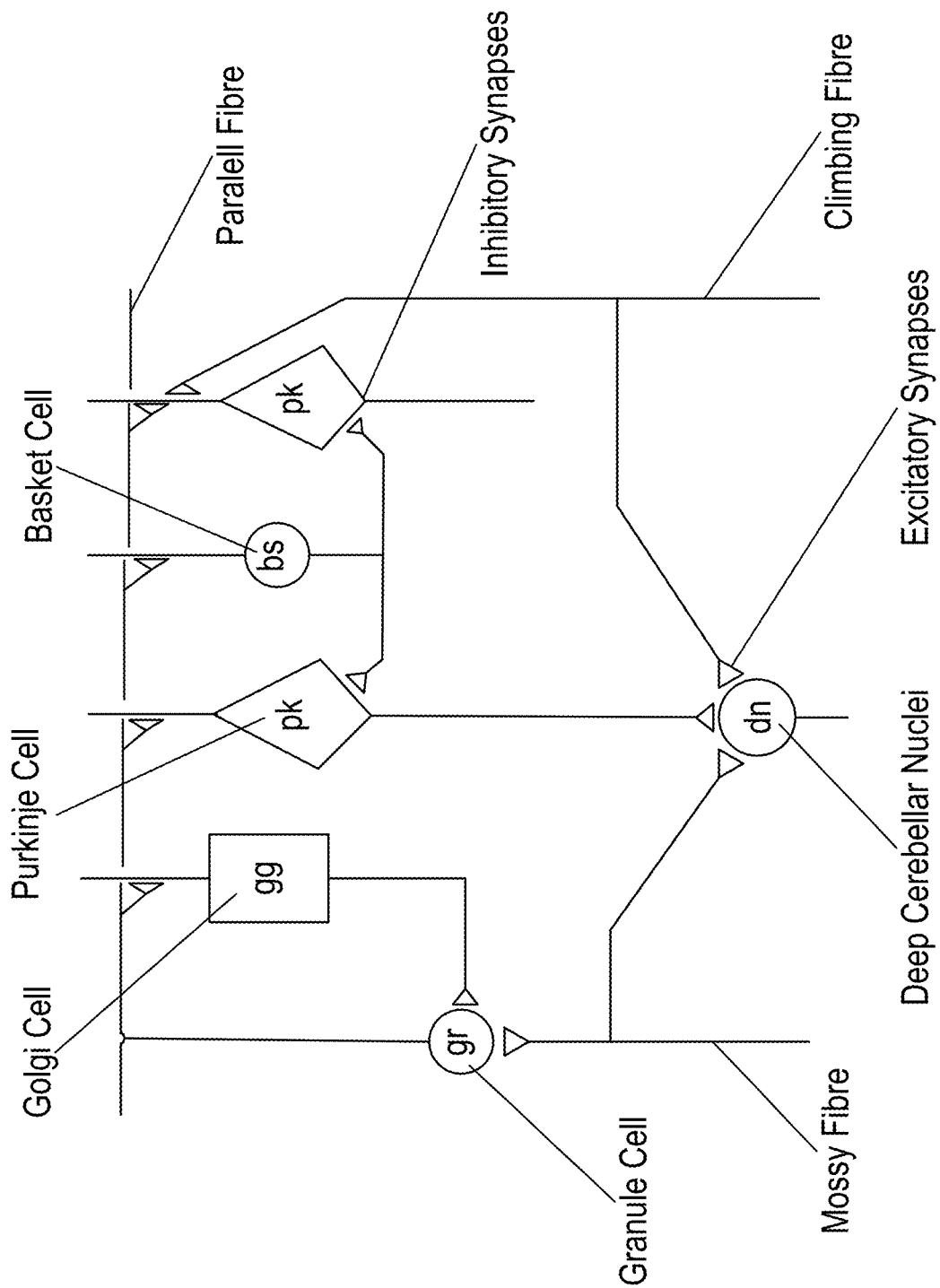
FIG. 5 schematically shows the neural circuits in the cerebellar cortex, linking the inputs to the outputs. The climbing fibers originate in the inferior olive, which itself receives inputs from the cerebral cortex, spinal cord and special senses (visual and auditory). Mossy fiber inputs originate from all other afferents such as vestibular afferents, spinal afferents, muscle spindles, golgi-tendon organs, joint receptors, skin receptors and the cerebral cortex. There are also three types of inhibitor interneurones in the intrinsic system, including basket cells, golgi cells and stellate cells. These are involved in lateral inhibition and in fine tuning of motor neuron function.
Figure 6:
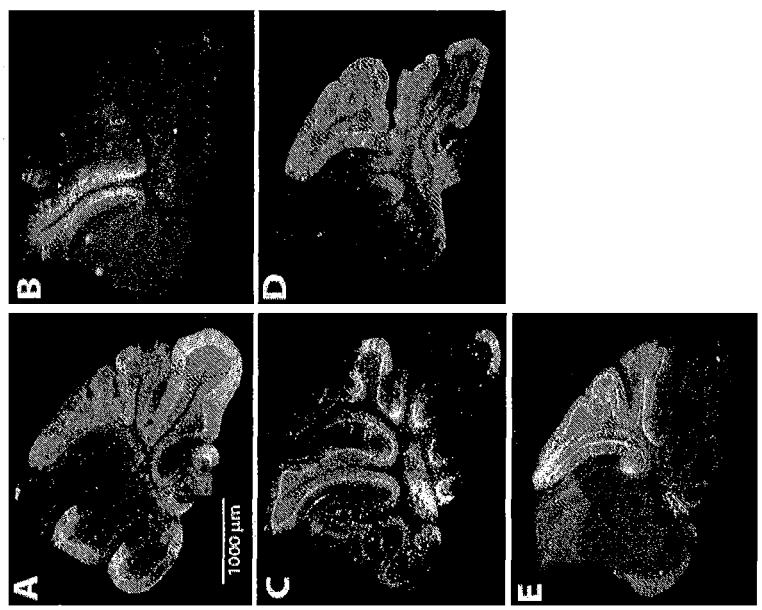
FIGS. 6A through 6E show human acid sphingomyelin ("hASM") immunopositive staining in sagittal cerebellar sections following injection of different AAV serotype vectors [(A)2/1, (B)2/2, (C)2/5, (D)2/7 and (E)2/8] encoding for human ASM into the deep cerebellar nuclei of ASMKO mice.
Figure 7:
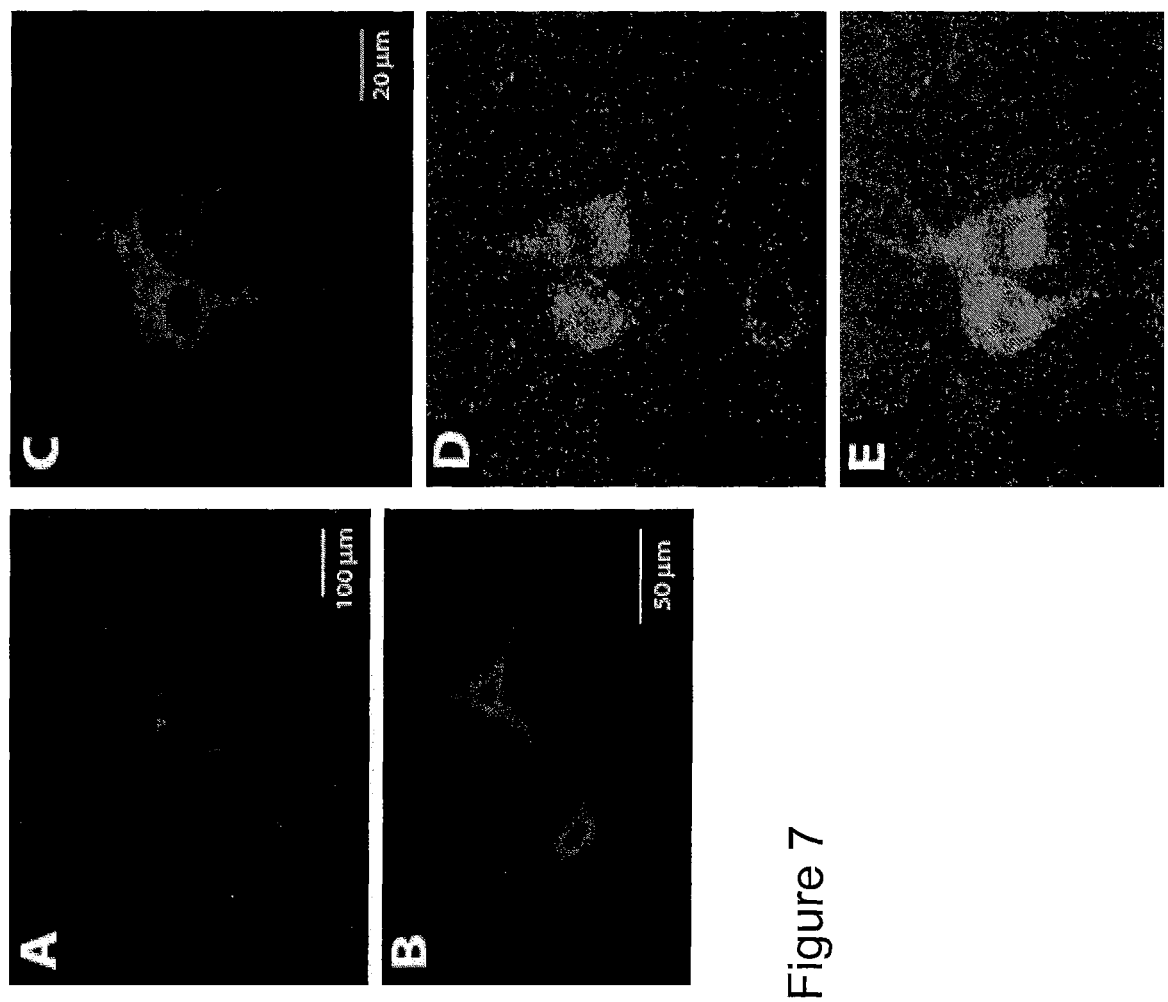
FIGS. 7A through 7E demonstrate human acid sphingomyelin ("hASM") protein transport to the spinal cord from the deep cerebellar nuclei. This effect was observed in mice treated with AAV2/2-ASM, AAV2/5-ASM, AAV2/7-ASM & AAV2/8-ASM (A) hASM 10× magnification; (B) hASM 40× magnification; (C) confocal hASM; (D) confocal ChAT; and (E) confocal hASM & ChAT.
Figure 8:
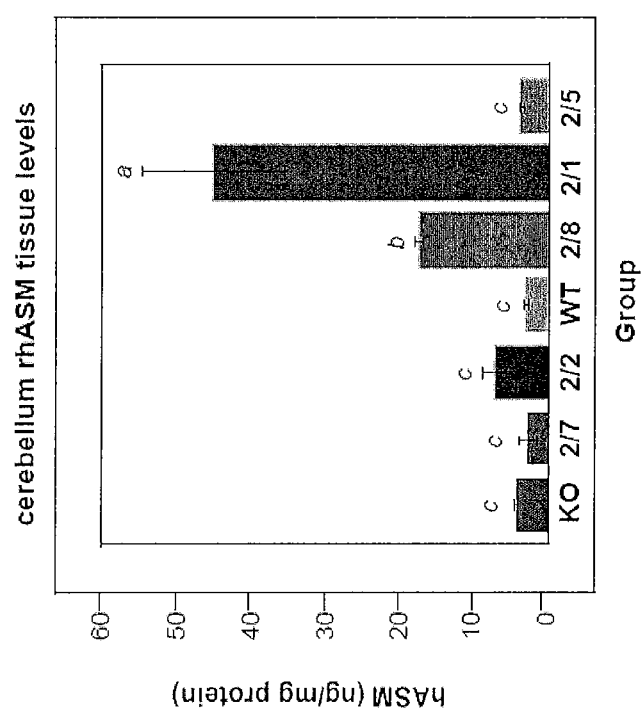
FIG. 8 graphically shows cerebellar tissue homogenate levels following injection of different AAV serotype vectors (2/1, 2/2, 2/5, 2/7 and 2/8) encoding for human ASM into the deep cerebellar nuclei (n=5/group). Groups not connected by the same letter are significantly ($p<0.0001$) different.
Figure 9:
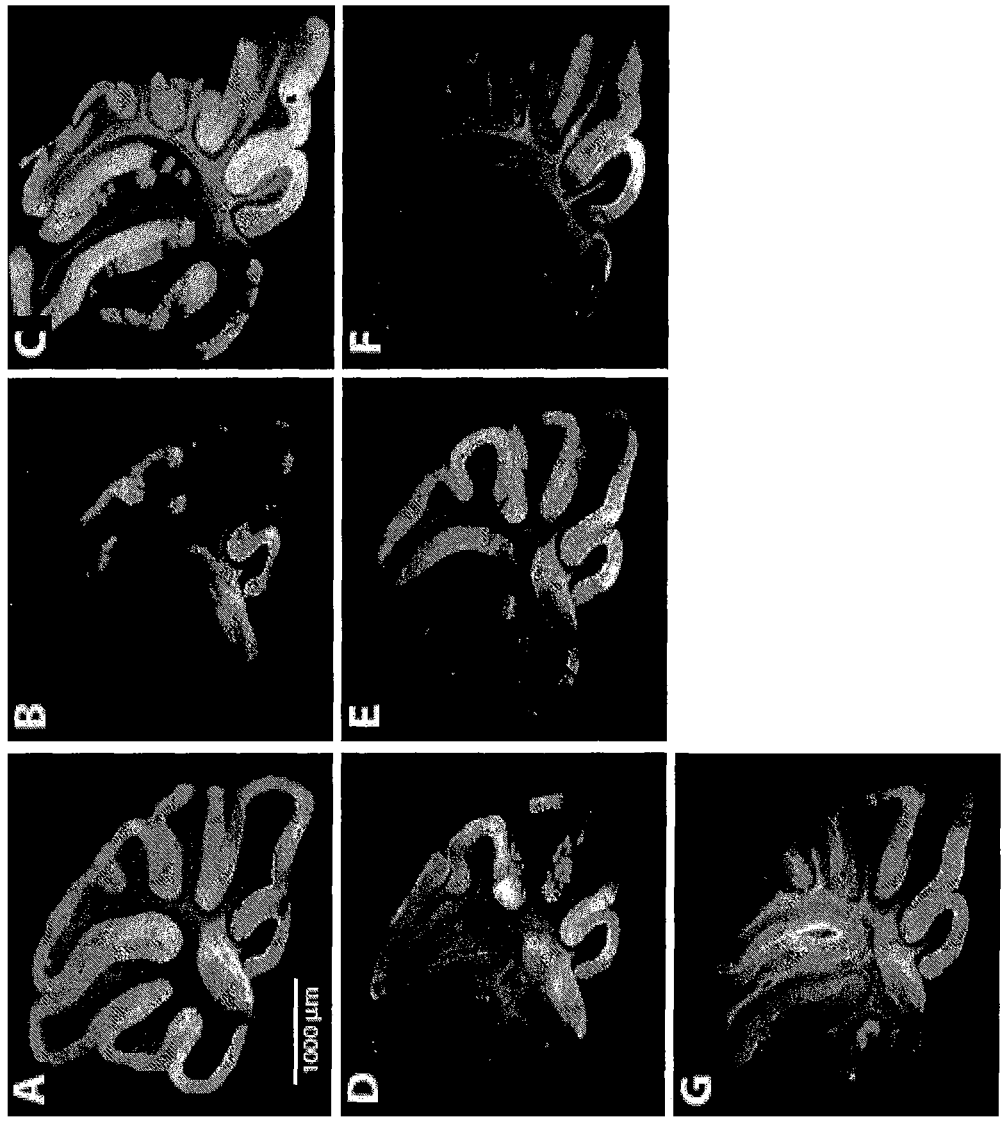
FIGS. 9A through 9G show calbindin immunopositive staining in sagittal cerebellar sections following injection of different AAV serotype vectors [(A)2/1, (B)2/2, (C)2/5, (D)2/7 and (E)2/8] encoding for human ASM into the deep cerebellar nuclei of ASMKO mice.

Deep within the cerebellum is grey matter called the deep cerebellar nuclei termed the medial (fastigial) nucleus, the interposed (interpositus) nucleus and the lateral (dentate) nucleus. As used herein, the term "deep cerebellar nuclei" collectively refers to these three regions. FIG. 2 schematically shows the three regions of the DCN. FIG. 4 schematically shows the major efferent (output) pathways from the DCN. FIG. 5 schematically shows the neural circuits in the cerebral cortex. FIGS. 12A and 12B schematically show connections between the DCN and the spinal cord or the brainstem, respectively.

If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

In one aspect, the disclosed methods include administering to the CNS of an afflicted subject a neurotropic viral vector carrying a transgene encoding a therapeutic product and allowing the transgene to be expressed within the CNS distally from the administration site at a therapeutic level. In addition, the vector may comprise a polynucleotide encoding for a biologically active molecule effective to treat the CNS disorder. Such biologically active molecules may comprise peptides including but not limited to native or mutated versions of full-length proteins, native or mutated versions of protein fragments, synthetic polypeptides, antibodies, and antibody fragments such as Fab' molecules. Biologically active molecules may also comprise nucleotides including single-stranded or double-stranded DNA polynucleotides and single-stranded or double-stranded RNA polynucleotides. For a review of exemplary nucleotide technologies that may be used in the practice of the methods disclosed herein, see Kurreck, (2003) J., Eur. J. Biochem. 270, 1628-1644 [antisense technologies]; Yu et al., (2002) PNAS 99(9), 6047-6052 [RNA interference technologies]; and Elbashir et al., (2001) Genes Dev., 15(2):188-200 [siRNA technology].

In an illustrative embodiment, the administration is accomplished by direct injection of a high titer vector solution into the DCN of a subject or patient. For example, the administration is by direct injection into one or more deep cerebellar nuclei region of the brain selected from the group consisting of the medial (fastigial) region, interposed (interpositus) region and the lateral (dentate) region. The DCN is an attractive site for injection due to its extensive efferent and afferent connections with the brainstem and spinal cord. These cells provide an efficient and minimally invasive means to deliver viral vector and expressed transgene to the spinal cord regions and the brainstem regions. Without being limited as to theory, the viral vector may be taken up by the axon terminals and transported retrogradely along the axon to the cell body of these neurons, which project throughout in the spinal cord region and/or brainstem. Cell bodies of neurons are also present in the DCN that have axon terminal endings that terminate, for example, in the cervical region of the spinal cord. Viral vector taken up by these cell bodies, or expressed transgene resulting from the viral vector or both, may be anterogradely transported to the axon terminal endings in the cervical spinal region. Therefore, by using the DCN as an injection site, only a small volume of viral vector is injected but this mediates significant transgene expression throughout one or more regions in the spinal cord and/or the brainstem.

In some embodiments, the methods comprise administration of a high titer neurotropic vector carrying a therapeutic transgene so that the transgene product is expressed at a therapeutic level in a second site within the CNS distal to the first site. In some embodiments, the viral titer of the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml). In further embodiments, the administration is accomplished by direct intraparenchymal injection of a high titer neurotropic vector solution into the diseased brain, thereafter the transgene is expressed distally, contralaterally or ipsilaterally, to the administration site at a therapeutic level at least 2, 3, 5, 8, 10, 15, 20, 25, 30, 35, 40, 45, or 50 mm from the administration site.

The distance between the first and the second sites is defined as the minimal distance region between the site of administration (first site) and the boundary of the detectable transduction of the distal site (second site) as measured using procedures known in the art or as described in the Examples, e.g., in situ hybridization. Some neurons in the CNS of larger mammals may span large distances by virtue of their axonal projections. For example, in humans, some axons may span a distance of 1000 mm or greater. Thus, in various methods of the invention, the vector can be axonally transported along the entire length of the axon at such a distance to reach and transduce the parent cell body.

A site of vector administration within the CNS is chosen based on the desired target region of neuropathology and the topology of brain circuits involved so long as an administration site and the target region have axonal connections. The target region can be defined, for example, using 3-D sterotaxic coordinates. In some embodiments, the administration site is chosen so that at least 0.1, 0.5, 1, 5, or 10% of the total amount of vector injected is delivered distally at the target region of at least 1, 200, 500, or 1000 $mm^3$. An administration site may be localized in a region innervated by projection neurons connecting distal regions of the brain. For example, the substantial nigra and bventral segmental area send dense projections to the caudate and putamen (collectively known as the striatum). Neurons within the substantial nigra and ventral tegmentum can be targeted for transduction by retrograde transport of AAV following injection into the striatum. As another example, the hippocampus receives well-defined, predictable axonal projections from other regions of the brain. Other administration sites may be localized, for example, in the spinal cord, brainstem (medulla, midbrain, and pons), mesencephalon, cerebellum (including the deep cerebellar nuclei), diencephalon (thalamus, hypothalamus), telencephalon (corpus striatum, cerebral cortex, or, within the cortex, the occipital, temporal, parietal or frontal lobes), or combinations thereof.

The second (target) site can be located any region of the CNS, including the brain and the spinal cord, that contains a neurons that project to the first (administration) site. In some embodiments, the second site is in a region of the CNS chosen from the substantia nigra, the medulla oblongata, the brainstem, or the spinal cord.

To deliver the vector specifically to a particular region of the central nervous system, especially to a particular region of the brain, it may be administered by sterotaxic microinjection. For example, on the day of surgery, patients will have the sterotaxic frame base fixed in place (screwed into the skull). The brain with sterotaxic frame base (MRIcompatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector in a pharmaceutically acceptable carrier will then be injected. The vector is then administered by direct injection to the primary target site and retrogradely transported to distal target sites via axons. Additional routes of administration may be used, e.g., superficial cortical application under direct visualization, or other non-stereotaxic application.

In addition because each region of the DCN targets specific regions of the CNS (see FIG. 1 and FIGS. 12A and 12B), one can specifically target the region of the CNS to which the transgene is delivered by pre-selecting the region of the DCN for administration. As is apparent to those of skill in the art, a multitude of dosing and targeted deliveries can be achieved by varying the location, sequence and number of transgene administrations. The total volume of material to be administered, and the total number of vector particles to be administered, will be determined by those skilled in the art based upon known aspects of gene therapy. Therapeutic effectiveness and safety can be tested in an appropriate animal model. For example, a variety of well-characterized animal models exist for LSDs, e.g., as described herein or in Watson et al. (2001) Methods Mol. Med. 76:383-403; or Jeyakumar et al. (2002) Neuropath. Appl. Neurobiol., 28:343-357 and ALS (see Tu et al. (1996) P.N.A.S. 93:3155-3160; Roaul et al. (2005) Nat. Med. 11(4):423-428 and Ralph et al. (2005) Nat. Med. 11(4):429-433).

In experimental mice, the total volume of injected AAV solution is for example, between 1 to 5 µl. For other mammals, including the human brain, volumes and delivery rates are appropriately scaled. For example, it has been demonstrated that volumes of 150 µl can be safely injected in the primate brain (Janson et al. (2002) Hum. Gene Ther. 13:1391-1412). Treatment may consist of a single injection per target site, or may be repeated along the injection tract, if necessary. Multiple injection sites can be used. For example, in some embodiments, in addition to the first administration site, a composition containing a viral vector carrying a transgene is administered to another site which can be contralateral or ipsilateral to the first administration site. Injections can be single or multiple, unilateral or bilateral.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Titration of Recombinant Vectors

AAV vector titers were measured according to genome copy number (genome particles per milliliter). Genome particle concentrations were based on Taqman® PCR of the vector DNA as previously reported (Clark et al. (1999) Hum. Gene Ther., 10:1031-1039; Veldwijk et al. (2002) Mol. Ther., 6:272-278). Briefly, purified AAV-ASM was treated with capsid digestion buffer (50 mM Tris-HCl pH 8.0, 1.0 mM EDTA, 0.5% SDS, 1.0 mg/ml proteinase K) at 50° C. for 1 hour to release vector DNA. DNA samples were put through a polymerase chain reaction (PCR) with primers that anneal to specific sequences in the vector DNA, such as the promoter region, transgene, or the poly A sequence. The PCR results were then quantified by a Real-time Taqman® software, such as that provided by the Perkin Elmer-Applied Biosystems (Foster City, Calif.) Prism 7700 Sequence Detector System.

Vectors carrying an assayable marker gene such as the β-galactosidase or green fluorescent protein gene (GFP) can be titered using an infectivity assay. Susceptible cells (e.g., HeLa, or COS cells) are transduced with the AAV and an assay is performed to determine gene expression such as staining of β-galactosidase vector-transduced cells with X-gal (5-bromo-4-chloro-3-indolyl-β-D-galactopyranoside) or fluorescence microscopy for GFP-transduced cells. For example, the assay is performed as follows: $4 \times 10^4$ HeLa cells are plated in each well of a 24-well culture plate using normal growth media. After attachment, i.e., about 24 hours later, the cells are infected with Ad type 5 at a multiplicity of infection (MOI) of 10 and transduced with serial dilutions of the packaged vector and incubated at 37° C. One to three days later, before extensive cytopathic effects are observed, the appropriate assay is performed on the cells (e.g., X-gal staining or fluorescence microscopy). If a reporter gene such as β-galactosidase is used, the cells are fixed in 2% paraformaldehyde, 0.5% glutaraldehyde and stained for β-galactosidase activity using X-gal. Vector dilutions that give well-separated cells are counted. Each positive cell represents 1 transduction unit (tu) of vector.

Expression of Functional Protein Deters Motor Impairment in a Therapeutically Relevant Mouse Model ASMKO mice are an accepted model of types A and B Niemann-Pick disease (Horinouchi et al. (1995) Nat. Genetics 10:288-293; Jin et al. (2002) J. Clin. Invest. 109:1183-1191; and Otterbach (1995) Cell 81:1053-1061). Niemann-Pick disease (NPD) is classified as a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem. 276:44976-44983; Slotte (1997) Subcell. Biochem. 28:277-293; and Viana et al. (1990) J. Med. Genet. 27:499-504.)

The following experiment, evaluated the relative ability of recombinant AAV2/1, AAV2/2, AAV2/5, AAV2/7 and AAV2/8 serotype vectors encoding human ASM (hASM) to express hASM protein, correct cholesterol storage pathology, undergo transport, rescue Purkinje cells, and initiate functional recovery in the ASMKO mouse after unilateral injection within the deep cerebellar nuclei. An additional group of ASMKO mice received bilateral injections into the DCN in order to assess whether increased transgene protein spread/expression would improve behavioral functional recovery.

Sixty-six male homozygous (−/−) acid sphingomyelinase knockout (ASMKO) mice and sixteen male wild type littermate controls were bred from heterozygote matings (+/−). Mice were genotyped by PCR following the procedure described in Gal et al. (1975) N Engl J Med:293:632-636. Mice from the original colony were backcrossed onto the C57/Bl6 strain. Animals were housed under 12:12 hour light:dark cycle and provided with food and water ad libitum. All procedures were performed under a protocol approved by the Institutional Animal Care and Use Committee.

After being anesthetized with isoflurane, mice (~7 weeks of age) were unilaterally injected into the deep cerebellar nuclei (A-P: −5.75 from bregma, M-L: −1.8 from bregma, D-V: −2.6 from dura, incisor bar: 0.0) with one of the following AAV serotype vectors (n=8/vector): AAV1-CMV-βgal, AAV1-CMV-ASM, AAV2-CMV-ASM, AAV5-CMV-ASM, AAV7-CMV-ASM, and AAV8-CMV-ASM. Vectors were delivered with a 10 μl Hamilton syringe mounted on a syringe pump at a rate of 0.5 μl/minute for a total of $1.86 \times 10^{10}$ genome particles per brain. The final injection volume for each vector was 4 μl. One hour before and twenty-four hours after surgery mice were given ketoprofen (5 mg/kg; SC) for analgesia.

Figure 10:
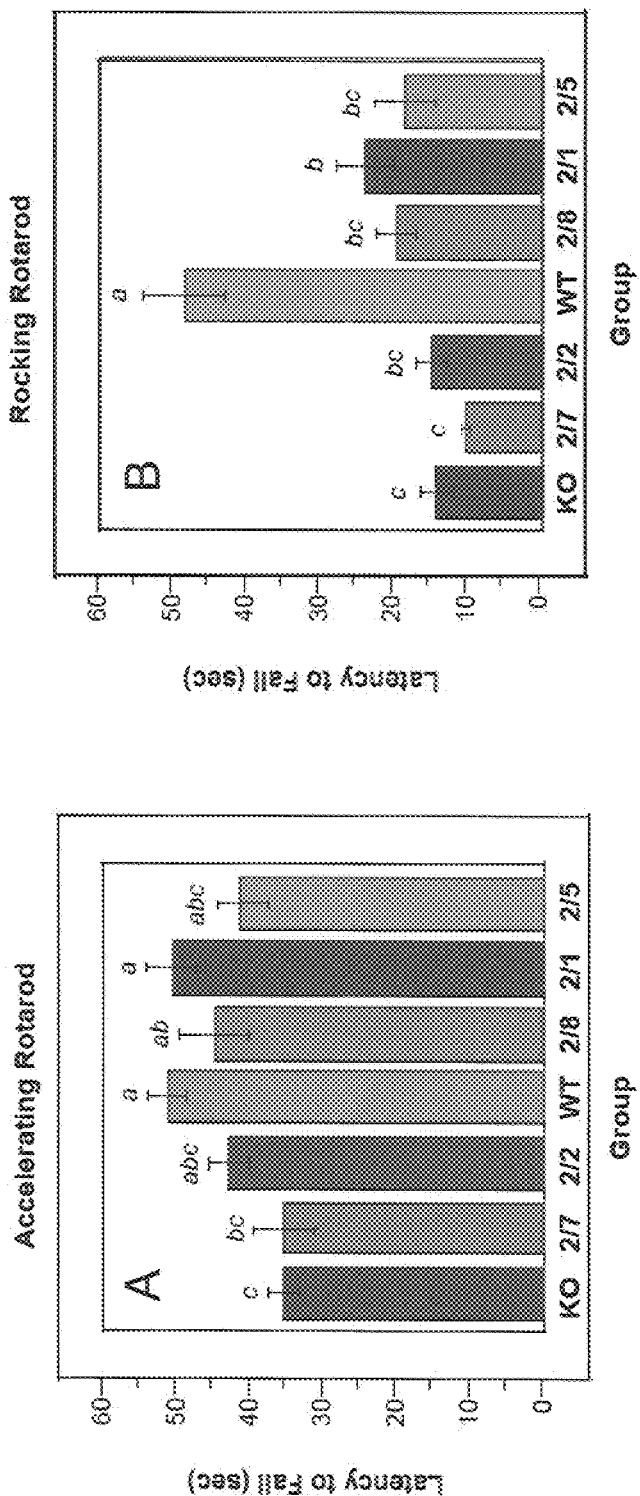
FIGS. 10A and 10B show accelerating and rocking rotarod performance (at 14 weeks of age) in ASMKO (injected with AAV-βgal), WT, and AAV-ASM treated ASMKO mice (n=8/group). Groups not connected by the same letter are significantly different. Mice injected with AAV2/1-ASM and AAV2/8-ASM demonstrated a significantly ($p<0.0009$) longer latency to fall than ASMKO mice injected with AAV2/1-βgal in the accelerating rotarod test. For the rocking rotarod test, mice injected with AA2/1-ASM demonstrated a significantly ($p<0.0001$) longer latency to fall than mice injected with AAV2/1-βgal.
Figure 11:
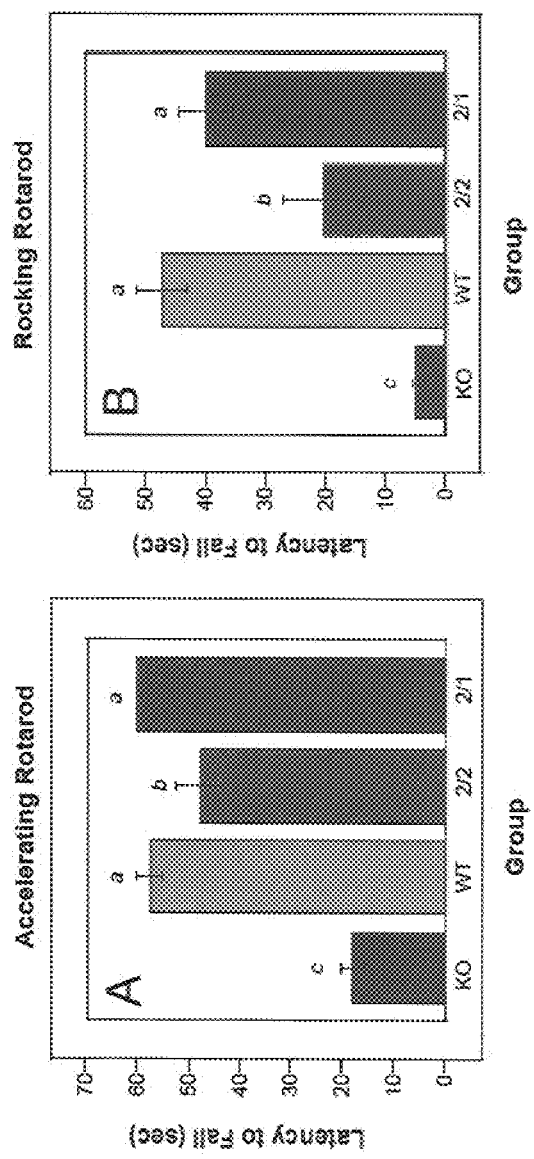
FIGS. 11A and 11B show rotarod performance in ASMKO (n=8), WT (n=8), and bilaterally AAV-ASM (n=5/group) treated mice (at 20 weeks of age). For both accelerating and rocking test, AAV-ASM treated mice performed significantly ($p<0.001$) better than ASMKO AAV2/1-βgal treated mice. Performance of mice injected with AAV2/1-ASM was indistinguishable from wild type mice in both the accelerating and rocking tests.

Mice were killed 7 weeks post-injection (14 weeks of age). At the time of sacrifice mice were overdosed with euthasol (150 mg/kg; IP) and rapidly decapitated (n=5/group) or transcardially perfused (n=3/group). Brains from decapitated mice were rapidly removed, snap frozen in liquid nitrogen, dissected into 3 sections (right cerebral hemisphere, left cerebral hemisphere, & cerebellum) homogenized, and analyzed for hASM by ELISA. Brains and spinal cords from perfused mice were processed for human ASM protein expression, cholesterol accumulation as detected by filipin staining, and Purkinje cell survival with calbindin staining on 50 μm vibratone sections. ASMKO mice that received bilateral injections (~7 weeks of age) of AAV2/1-βgal (n=8), AAV2/1-ASM (n=5), and AAV2/2-ASM (n=5) were sacrificed at 20 weeks of age after undergoing rotarod testing. Mice were tested by accelerating and rocking rotarod for motor function on the Smartrod (AccuScan) using methods known in the art. Exemplary methods are reproduced in Sleat et al. (2004) J. Neurosci. 24:9117-9126. FIGS. 10 and 11 graphically show the results of rotarod tests as a measurement of recovery of motor function.

The full-length human ASM cDNA under the control of the human cytomegalovirus immediate-early (CMV) promoter, with an SV40 polyadenylation sequence, and a hybrid intron, was cloned into a plasmid containing ITRs from AAV serotype 2 (AAV2 ITR). Jin et al. (2002) J Clin Invest. 109:1183-1191. Hybrid vectors were produced by triple transfection using a series of helper plasmids containing serotype specific capsid coding domains in addition to the AAV type 2 replication genes. This strategy allows the packaging of AAV2 ITR vectors into each serotype-specific virion Rabinowitz, et al. (2002) J. Virol. 76:791-801. With this approach the hASM recombinant genome was used to generate a series of rAAV-hASM vectors of various serotypes including AAV2/1, AAV2/2, AAV2/5, AAV2/7 and AAV2/8. Recombinant AAV vectors were purified by ion-exchange chromatography (Serotypes 2/1, 2/2 and 2/5). O'Riordan et al. (2000) J Gene Med 2: 444-54 or CsCl centrifugation (serotypes 2/8 and 2/7) Rabinowitz et al. (2002) J. Urrol. 76:791-801. The final titer of AAV-ASM virion particles (DNAse-resistant particles), was determined by TaqMan PCR of the CMV sequence. Clark et al. (1999) Hum. Gene Therapy 10:1031-1039.

Human ASM antibodies are human specific and do not cross react with mouse ASM. Coster (Corning, N.Y.) 9018 plates coated (100 μl/well) with monoclonal recombinant human ASM (rhASM) antibody (2 μg/ml) diluted in 50 mM sodium carbonate buffer (pH 9.6) were incubated overnight @ 2-8° C. Excess coating antibody was removed and blocking diluent (KPL, Inc., MD) was added for 1 h @ 37° C. Plates were washed with a microplate washer (Molecular Devices, CA) for two cycles. Standards, controls and samples diluted in standard dilution buffer (PBS, 0.05% Tween, 1% HP-BSA) were pipetted in duplicate and allowed to incubate for 1 h @ 37° C. Plates were washed as described above. One hundred microliters of biotinylated recombinant human ASM (rhASM) antibody (diluted 1:20 K in standard dilution buffer) was added to each well, allowed to incubate for 1 h @ 37° C., and then removed with a microplate washer. Streptavidin-HRP (Pierce Biotechnology, Inc., IL) diluted 1:10 K was then added (100 μl/well) and allowed to incubate for 30 min at room temperature. Plates were washed as described above and then incubated with Sure-Blue TMB (KPL, Inc., MD) for 15 minutes @ 36-38° C. The reaction was stopped with stop solution (KPL, Inc., MD) and absorbance values were then read at 450 nm with a Spectra Max 340 plate reader (Molecular Devices, CA). Data analysis was completed using Softmax Pro 4.3 software (Molecular Devices, CA).

The protein concentration for each sample was determined with a BCA protein assay kit (Pierce Biotechnology, Inc., IL) using bovine serum albumin as standard.

Mice were transcardially perfused with fixative containing 2% paraformaldehyde, 0.03% glutaraldehyde, 0.002% $CaCl_2$ in 0.1 M sodium acetate buffer at pH 6.5, followed by perfusion with the same fixative at pH 8.5. Mouse brains and spinal cords were dissected and post-fixed overnight at 4° C. in pH 8.5 fixative without glutaraldehyde. The tissues were washed in 0.1 M potassium phosphate buffer, pH 7.4, embedded in 3.5% agar and cut into 50 μm sagittal sections with a vibratome.

Brains and spinal cords were vibratome-sectioned sagittally at 50 μm intervals. Sections were processed for immunofluoresence with primary antibodies against human ASM (1:200). Sections were incubated in 10% donkey serum, 0.3% Triton X-100 in PBS for 1 hour, followed by incubation with biotinylated mouse anti-human ASM in 2% donkey serum, 0.2% Triton X-100 in PBS for 72 hours. After washing, the signal was amplified using a Tyramide Signal Amplification kit (PerkinElmer, Boston Mass.). Human ASM protein was visualized with a Nikon fluorescent microscope, and images were captured with a SPOT camera and Adobe Photoshop software.

Filipin Complex (Sigma, St. Louis, Mo.) was first diluted in 100% methanol for a stock concentration of 1 mg/ml. Stock solution is stable for 4 weeks at −20° C. After washing with PBS, the sections were incubated in the dark for three hours in a freshly made 10 µg/ml filipin solution in PBS. Sections were then washed three times with PBS. Cholesterol deposits were visualized under an ultraviolet filter on a fluorescence microscope.

Brains were processed for immunofluorescence using primary antibodies directed against the calcium binding protein, calbindin. Sections were washed with potassium phosphate buffer (KPB) and then rinsed with potassium phosphate buffered saline (KPBS). Sections were then blocked in 5% donkey serum, 0.25% Triton X-100 in KPBS for up to 3 hours and then incubated in 5% donkey serum, 0.2% Triton X-100 and mouse anti-calbindin (1:2500, Sigma, St. Louis, Mo.) in KPBS. After 72 hours at 4° C. sections were rinsed with KPBS with 0.1% Triton X-100 three times. Secondary antibody, donkey-anti mouse CY3 (1:333, Jackson Immunoresearch Laboratories, West Grove, Pa.) was added in KPBS+0.1% Triton X-100 for 90 minutes at room temperature. Sections were washed with KPB and then mounted onto gel-coated slides. Calbindin-positive cells were visualized under epifluorescence. In order to quantify Purkinje cells of the cerebellum, four full-faced, medial cerebellar sections were selected from each animal. Calbindin-immunopositive Purkinje cells were viewed under a fluorescent microscope and cell bodies were counted at a magnification of 20×. Each lobe was counted separately. Two separate focal planes were counted per lobe. Only cells in focus were counted to insure that no cell was counted twice.

Fifty (50) µm vibratome sections were first processed for immunofluorescence with antibodies directed against human ASM, as described above. The sections were then washed in PBS and stained for choline acetyltransferase (ChAT; rabbit polyclonal, 1:500, Chemicon International, Temecula, Calif.) with the protocol outlined above for calbindin. Rather than using a CY3 secondary antibody, however, donkey-anti-rabbit FITC (1:200, Jackson Immunoresearch Laboratories, West Grove, Pa.) was used. The staining was first visualized under epifluorescence and later images were acquired with a confocal microscope.

Filipin staining was quantified as follows. Exposure-matched images were captured using a Nikon E600 wide field upright epifluorescence microscope equipped with a SPOT digital camera. The AAV2/1-β-gal group was imaged first, and that exposure was used to acquire all additional images. Each image analyzed represents a medial sagittal plane through the length of each half-brain. Morphometric analysis was performed with Metamorph software (Universal Imaging Corporation). The AAV2/1-β-gal images were thresholded; once established, the same threshold was used in all images. The following regions were manually selected by the user and analyzed separately: cerebellum, pons, medulla, midbrain, cerebral cortex, hippocampus, thalamus, hypothalamus and striatum. Integrated intensity was measured in each region, and all measurements (n=3/group) from a given group of animals were used to generate averages. The reduction in cholesterol in the treated animals was then calculated as the percent decrease of the integrated intensity compared to the knockout β-gal injected mice. Positive hASM immunostaining was observed throughout the cerebellum (Table 1), pons, medulla and spinal cord following unilateral injection of AAV-ASM within the deep cerebellar nuclei.

TABLE 1

Areas with positive hASM staining as function of AAV serotype.

| Structure | AAV1 | AAV2 | AAV5 | AAV7 | AAV8 |
|---|---|---|---|---|---|
| deep cerebellar nuclei | ++++ | ++ | +++ | +++ | ++++ |
| cerebellar lobules | ++++ | ++ | +++ | +++ | ++++ |
| pons | ++ | ++ | ++ | ++ | + |
| medulla | + | ++ | ++ | +++ | + |
| spinal cord |  | +++ | +++ | ++ | + |
| thalamus | * | * | * | * | * |
| hypothalamus | * | * | * | * | * |
| hippocampus | * | * | * | * | * |
| striatum | * | * | * | * | * |
| cerebral cortex | * | * | * | * | * |

* indicates positive hASM was below limit of detection, but correction of cholesterol pathology still occurred Within the cerebellum mice treated with AAV2/1-ASM and had the most widespread (i.e., spread between lobules within the same sagittal section) level of hASM expression, whereas mice treated with AAV2/2-ASM had the most restricted level of Human ASM protein expression. Human ASM protein expression in mice treated with AAV2/5-ASM, AAV2/7-ASM, and AAV2/8-ASM was intermediate between these two groups. Medial-lateral spread between sagittal sections was maximal in mice treated with serotypes 1 & 8 and minimal is mice injected with serotype 2. Serotypes 5 & 7 initiated medial-lateral spread patterns intermediate between serotypes 1 and 2. Each layer of the cerebellum (i.e., molecular, Purkinje and granular) was transduced by each AAV serotype; however, an increased affinity for the molecular layer was apparent for all serotypes. Purkinje cell transduction was maximal in mice treated with serotypes 1 and 5. Mice injected with serotype 7 had the fewest number of transduced Purkinje cells. Mice treated with serotype 8 also had few transduced Purkinje cells, but had less ASM expression within the granular layer when compared to serotypes 1, 2, 5 & 7. Purkinje cells transduced with ASM appeared to have a healthy cytostructure. Quantitative analysis of AAV mediated hASM protein expression by ELISA in cerebellar tissue homogenates supports these immunohistochemical findings. Mice injected with serotypes 1 and 8 demonstrated significantly ($p<0.0001$) higher cerebellum hASM protein levels when compared to all other mice. Cerebellar hASM levels from mice injected with serotypes 2, 5, & 7 were not above WT levels (i.e. background). As expected human ASM was not detected in wild type mice—the hASM antibody used in the ELISA are human specific.

An absence of functional ASM protein results in lysosomal accumulation of sphingomyelin, and subsequent secondary metabolic defects such as abnormal cholesterol trafficking. Sarna et al. Eur. J. Neurosci. 13:1873-1880 and Leventhal et al. (2001) J. Biol. Chem. 276:44976-4498. Free cholesterol buildup in the ASMKO mouse brain is visualized suing filipin, an autofluorescent molecule isolated from *streptomyces* filipinensis. Wild-type mouse brains do not stain positively for filipin. In all AAV treated mice (with exception to MV2/1-βgal) clearance of filipin staining (Table 2) overlapped with areas that were positive for hASM immunostaining indicating that each serotype vector is capable of generating a functional transgene product.

TABLE 2

Percent Reduction in Filipin (i.e., cholesterol) clearance as compared to ASMKO mice treated with AAV-βgal in selected brain regions following intracerebellar injection of different AAV serotypes (n = 3/serotype; 2/1, 2/2, 2/5, 2/7, and 2/8) encoding for human ASM into the deep cerebellar nuclei of ASMKO mice.

| | 2/1 | 2/2 | 2/5 | 2/7 | 2/8 |
|---|---|---|---|---|---|
| Cerebellum | 96.54 ± 2.14 | 93.85 ± 1.257 | 86.75 ± 9.58 | 96.47 ± 1.93 | 99.12 ± .66 |
| Midbrain | 96.72 ± 1.73 | 53.08 ± 22.89 | 65.88 ± 24.53 | 73.39 ± 22.39 | 91.10 ± .105 |
| Pons | 91.31 ± 5.80 | 50.07 ± 21.26 | 70.96 ± 25.60 | 93.15 ± 31.20 | 96.72 ± 1.20 |
| Medulla | 93.29 ± 6.22 | 88.46 ± 3.04 | 81.55 ± 17.31 | 80.73 ± 14.99 | 97.40 ± 1.60 |
| Thalamus | 48.88 ± 25.25 | 41.21 ± 27.35 | 34.86 ± 16.67 | 48.44 ± 28.65 | 77.03 ± 12.08 |
| Hypothalamus | 82.81 ± 10.14 | 86.96 ± 12.93 | 88.46 ± 5.90 | 82.95 ± 11.46 | 99.68 ± .31 |
| Cortex | 27.60 ± 24.75 | 73.62 ± 14.9 | 55.65 ± 28.89 | 76.97 ± 14.27 | 98.30 ± .34 |

As previously demonstrated by (Passini et al. (2003) in "Society for Neuroscience" New Orleans, La.), filipin clearance also occurred in areas anatomically connected with the injection site, but that did not stain positively for hASM. MetaMorph analysis indicated that a reduction in filipin staining occurred throughout the entire rostral caudal axis. In the cerebellum and brainstem filipin was maximally reduced in mice treated with AAV2/1-ASM and AAV2/8-ASM, whereas in the diencephalon and cerebral cortex mice injected with AAV2/8-ASM had the best overall level of filipin clearance (Table 2). Nevertheless, these results indicate that the level of hASM required to correct cholesterol storage pathology is the ASMKO mouse CNS is minimal (i.e., below the hASM immunoflourescence limit of detection).

Histological studies indicate that the ASMKO mouse cerebellum undergoes rapid deterioration. More specifically, Purkinje cells progressively die off between 8 and 20 weeks of age (Sarna et al. (2001) Eur. J. Neurosci. 13:1813-1880 and Stewart et al. (2002) in "Society for Neuroscience" Orlando, Fla.). Calbindin is a widely accepted Purkinje cell maker. Positive calbindin staining in AAV-ASM treated mice would suggest that AAV mediated expression of hASM is therapeutic. Overall our results indicate that AAV mediated hASM expression in the cerebellum prevents Purkinje cell death in the ASMKO mouse (Table 3). As expected Purkinje cell survival did not occur in lobules I-III; mice were injected at 7 weeks of age and by 8 weeks the majority of these cells have already died off. Purkinje cell survival in lobules IV/V was maximal in mice treated with serotype 1. In lobule VI no significant Purkinje cell survival was observed in AAV treated mice. In lobule VII only mice treated with serotype 5 showed significant Purkinje cell survival. In lobule VIII again mice treated with serotype 5 as well as serotype 2 showed significant Purkinje cell survival. In lobules IX and X there were no significant differences between WT and KO mice (or between AAV treated mice) in Purkinje cell counts. This was expected, because at 14 weeks of age (i.e., age at sacrifice) Purkinje cells in these lobules are still viable in ASMKO mice. Across all lobules Purkinje cell survival was maximal in mice treated with serotypes 1, 2, & 5 and minimal in mice treated with serotypes 7 & 8.

TABLE 3

Purkinje cell counts in cerebellar lobules I-X in WT and ASMKO mice following intracerebellar injection of different AAV serotypes (n = 3/serotype; 2/1, 2/2, 2/5, 2/7, and 2/8) encoding for human ASM into the deep cerebellar nuclei of ASMKO mice.

| | 2/1 | 2/2 | 2/5 | 2/7 | 2/8 | KO | WT |
|---|---|---|---|---|---|---|---|
| I/II | 7.42 ± 9.80 | 4.5 ± 10.58 | 9.40 ± 11.59 | 12.33 ± 10.58 | 1 ± 9.16 | 5.8 ± 11.59 | 113 ± 10.58 |
| III | 12.42 ± 10.32 | 11.33 ± 11.14 | 26.80 ± 12.21 | 15.33 ± 11.14 | 9.8 ± 12.21 | 2 ± 9.65 | 147.50 ± 11.14 |
| IV/V | 60.57 ± 17.28 | 36.5 ± 18.67 | 27.80 ± 20.45 | 29.66 ± 18.67 | 6.8 ± 20.45 | 8 ± 16.16 | 220.66 ± 18.67 |
| VI | 61.14 ± 11.21 | 27.5 ± 12.11 | 72.20 ± 13.26 | 31.16 ± 12.11 | 3.8 ± 13.26 | 68.5 ± 10.48 | 121.16 ± 12.11 |
| VII | 17.42 ± 4.15 | 37.66 ± 4.49 | 40.60 ± 4.91 | 5.33 ± 4.49 | .2 ± 4.95 | 17.37 ± 3.88 | 37.16 ± 4.49 |
| VIII | 44.14 ± 10.75 | 48.66 ± 11.62 | 82.80 ± 12.73 | 11.33 ± 11.62 | 18.40 ± 12.73 | 35.12 ± 10.06 | 103.33 ± 11.62 |
| IX | 126.28 ± 19.17 | 102.66 ± 20.71 | 136.40 ± 22.68 | 60.16 ± 20.71 | 84.40 ± 22.68 | 108.0 ± 17.93 | 144 ± 20.71 |
| X | 89.85 ± 12.54 | 76.83 ± 13.55 | 93.80 ± 14.84 | 48.16 ± 13.55 | 64.80 ± 14.84 | 87 ± 11.73 | 86.66 ± 13.55 |

Numbers appearing bold italic are significantly different from KO mice (i.e., mice treated with AAV2/1-βgal) p ≤ .01.

On the accelerating rotarod test mice unilaterally injected with AAV2/1-ASM and AAV2/8-ASM demonstrated a significantly (p<0.0009) longer latency to fall than ASMKO mice injected with MV2/1-βgal. Mice injected with serotype AA2/1-ASM were not significantly different from wild type mice. Mice injected with AAV2/2-ASM and AAV2/5-ASM showed a trend for a longer latency to fall than ASMKO mice injected with AAV2/1-βgal; whereas, mice injected with AAV2/7-ASM did not. For the rocking rotarod test, only mice injected with AA2/1-ASM demonstrated a significantly (p<0.0001) longer latency to fall than mice injected with AA2/1-βgal. In this case wild type mice performed significantly better than mice injected with AA2/1-ASM. ASMKO mice that received bilateral injection of either AAV2/1-ASM or AAV2/2-ASM performed significantly (p<0.001) better than ASMKO AAV2/1-βgal treated mice for both accelerating and rocking tests. AAV2/1-ASM bilaterally injected mice performed comparably to wild type mice for both tests.

One way to determine if AAV generated hASM is functionally active within the ASMKO CNS is to assess its influence on cholesterol storage pathology—a secondary metabolic defect of NPA disease. In all AAV treated mice (with exception to AAV2/1-βgal) correction of cholesterol storage pathology overlapped with areas that were positive for hASM immunostaining indicating that each serotype vector is capable of generating a functional transgene product. As previously demonstrated, correction of abnormal cholesterol metabolism correction also occurred in areas anatomically connected with the injection site, but also in regions that did not stain positively for hASM, suggesting that the level hASM required for correction of cholesterol storage pathology is minimal. Consistent with these hASM histochemical and biochemical results, mice treated with serotypes 1 and 8 demonstrated a marked reduction in cholesterol storage pathology. Mice treated with serotypes 2, 5, & 7 also showed a reduction in cholesterol storage pathology, but not to the same extent as mice treated with serotypes 1 & 8.

Therapeutically Relevant Model of Amyotrophic Lateral Sclerosis (ALS).

Amytrophic lateral sclerosis (ALS) is a fatal neurodegenerative disease that is characterized by a selective loss of motor neurons in the cortex, brain stem and spinal cord. Progression of the disease can lead to atrophy of limb, axial and respiratory muscles. Motor neuron cell death is accompanied by reactive gliosis, neurofilament abnormalities, and a significant loss of large myelinated fibers in the corticospinal tracts and ventral roots[1-6]. Although the etiology of ALS is poorly understood, accumulating evidence indicates that sporadic (SALS) and familial (FALS) ALS share many similar pathological features; thus, providing a hope that the study of either form will lead to a common treatment 7. FALS accounts for approximately 10% of diagnosed cases, of which 20% are associated with dominantly inherited mutations in Cu/Zn superoxide dismutase (SOD1)[8]. Transgenic mice that express the mutant human SOD1 protein (e.g., SOD1$^{G93A}$ mice) recapitulate many pathological features of ALS and are an available animal model to study ALS[9]. For SALS, a myriad of pathological mechanisms have been implicated as the underlying cause, including glutamate induced excitotoxicity, toxin exposure, proteasome dysfunction, mitochondrial damage, neurofilament disorganization and loss of neurotrophic support[10,11].

To date there is no effective therapy for the treatment of ALS. Neurotrophic factors such as insulin growth factor I (IGF-1) have been investigated extensively for their potential usefulness in the treatment of ALS. Intracranial delivery of viral vectors (that are capable of axonal transport) to regions of the CNS that are interconnected with brainstem and spinal motor neurons provides a means of administering potential therapeutics, such as IGF-1, to areas that would otherwise be difficult to target through prior art means.

Without being limited as to theory, it is may be that these targeted regions will not necessarily need to have direct connections with motor neurons; that is, it may be sufficient for these targeted regions to have direct connections with cells (e.g., interneurons and astrocytes) that merely compose the motor neuron's cellular environment. This supposition is supported by studies in chimeric mice that are mixtures of normal and SOD1 mutant-expressing cells. These experiments showed that non-neuronal cells that did not express mutant SOD1 delayed degeneration and significantly extend survival of mutant-expressing motor neurons[13]. Furthermore, additional experiments have demonstrated that cells that make up the cellular environment of a motor neuron (e.g., astrocytes and microglia) are important sources of neurotrophic factors, and damage to these cells (as occurs pathologically in ALS) has been suggested to be one of the underlying factors that contributes to motor neuron degeneration[11].

A region of the CNS that is likely to support the transport of a therapeutic viral vector and/or expressed protein to the cellular environment of motor neurons is the deep cerebellar nuclei (DCN) of the cerebellum. The DCN has extensive afferent and efferent connections both with the brainstem and spinal cord (see FIG. 1)[14-19]. Targeting the DCN in a mouse model of neurometabolic disease with viral vectors capable of axonal transport resulted in detection of transgene protein in both the brain stem and spinal cord[20]. Interestingly transgene protein was detected in cells that were both positive and negative for choline acetyltransferase (ChAT), a motor neuron marker.

Overexpression of superoxide dismutase-1 (SOD1) gene mutations in mice and rats recapitulates the clinical and pathological characteristics of ALS in humans. Compounds active in retarding symptoms in this model have been shown to be predictive for clinical efficacy in patients with ALS, and therefore is a therapeutically relevant model of this disease. Such mouse models have been previously described in Tu et al. (1996) P.N.A.S. 93:3155-3160; Kaspar et al. (2003) Science 301:839-842; Roaul et al. (2005) Nat. Med. 11(4):423-428 and Ralph et al. (2005) Nat. Med. 11(4):429-433.

The current experiments, therefore, sought to investigate the influence of bilateral DCN delivery of AAV-IGF-1 on disease progression in symptomatic (i.e., 90 day old) SOD1$^{G93A}$ mice. Specifically, the primary goals were to determine if delivery of AAV-IGF-1 resulted in (1) vector and/or protein delivery to the brainstem and spinal cord; (2) a reduction in neuropathology in the brainstem and spinal cord; (3) improvement in motor behavioral function; and (4) a significant extension of lifespan. The results indicate that injection of viral vectors to regions of the CNS that are interconnected with the brainstem and spinal cord is a viable approach for delivering potential therapeutic transgenes to the brainstem and spinal cord. Moreover, our results support the development of therapies that are designed to treat motor neuron degeneration through modification of their cellular environment.

Two studies were performed in the G93A SOD1 (SOD1$^{G93A}$ mutant mouse, referred to here at the SOD1 mouse). This model closely mimics human ALS. There is progressive motor neuron degeneration with hindlimb motor deficits appearing around 90 days of age in the mouse. Death occurs around days 120-122. Each study had four treatment groups: 1) mice received AAV serotype 1 encoding for IGF-1 (AAV1-IGF-1); 2) mice received AAV serotype 1 encoding for green fluorescent protein (AAV1-GFP); 3) mice received AAV serotype 2 encoding for IGF-1 (AAV2-IGF-1); and 4)) mice received AAV serotype 2 encoding for green fluorescent protein (AAV2-GFP).

Without being limited as to theory, IGF-1 is a therapeutic protein for the treatment of ALS due to its many actions at different levels of neuraxis (see Dore et al., Trends Neurosci, 1997, 20:326-331). In the brain: It is thought to reduce both neuronal and glial apoptosis, protect neurons against toxicity induced by iron, colchicine, calcium destabilizers, peroxides, and cytokines. It also is thought to modulate the release of neurotransmitters acetylcholine and glutamate. It is also thought to induce the expression of neurofilament, tublin, and myelin basic protein. In the spinal cord: IGF-1 is thought to modulate ChAT activity and attenuate loss of cholinergic phenotype, enhance motor neuron sprouting, increase myelination, inhibit demyelination, stimulate motor neuron proliferation and differentiation from precursor cells, and promote Schwann cell division, maturation, and growth. In the muscle: IGF-1 is thought to induce acetylcholine receptor cluster formation at the neuromuscular junction and increase neuromuscular function and muscle strength. In this experiment, the IGF-1 Ea form of the protein was utilized.

Green fluorescent protein was utilized as a control protein, which also enabled the visualization of expression mediated by the injection of the AAV vectors.

Ninety days after birth, SOD1 mice were injected bilaterally into the DCN with the AAV recombinant vectors. In one study, the dose was approximately 2.0 e10 gc/ml injected per site. Certain mice were sacrificed about 110 days after birth and their brain and spinal cord were analyzed for GFP staining, IGF-1 expression via immunohistochemistry, IGF-1 expression via ELISA, IGF-1 expression via RT-PCR, ChAT localization via immunohistochemistry, glial fibrillary acidic protein (GFAP) expression, motor neuron counts, functional testing (rocking and accelerating) on the rotarod as described above, grip strength of both the forelimb and hindlimb using a grip strength meter, and survival.

A "death event" was entered when animals could no longer "right" themselves within 30 seconds after the animal was placed on its back, or animals were found dead by animal care technicians. "Death event" classification was performed by 2 individuals with the animal's group (GFP vs. IGF-1 being blinded) at time of assessment.

Figure 13:
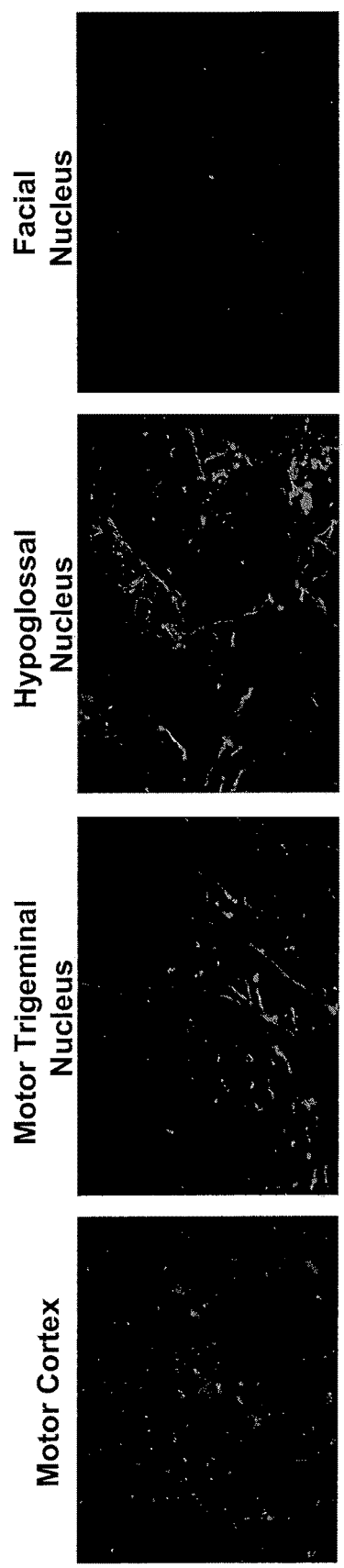
FIG. 13 illustrates green fluorescent protein distribution in the brainstem, or upper motor neurons, following DCN delivery of AAV encoding for green fluorescent protein (GFP).
Figure 14:
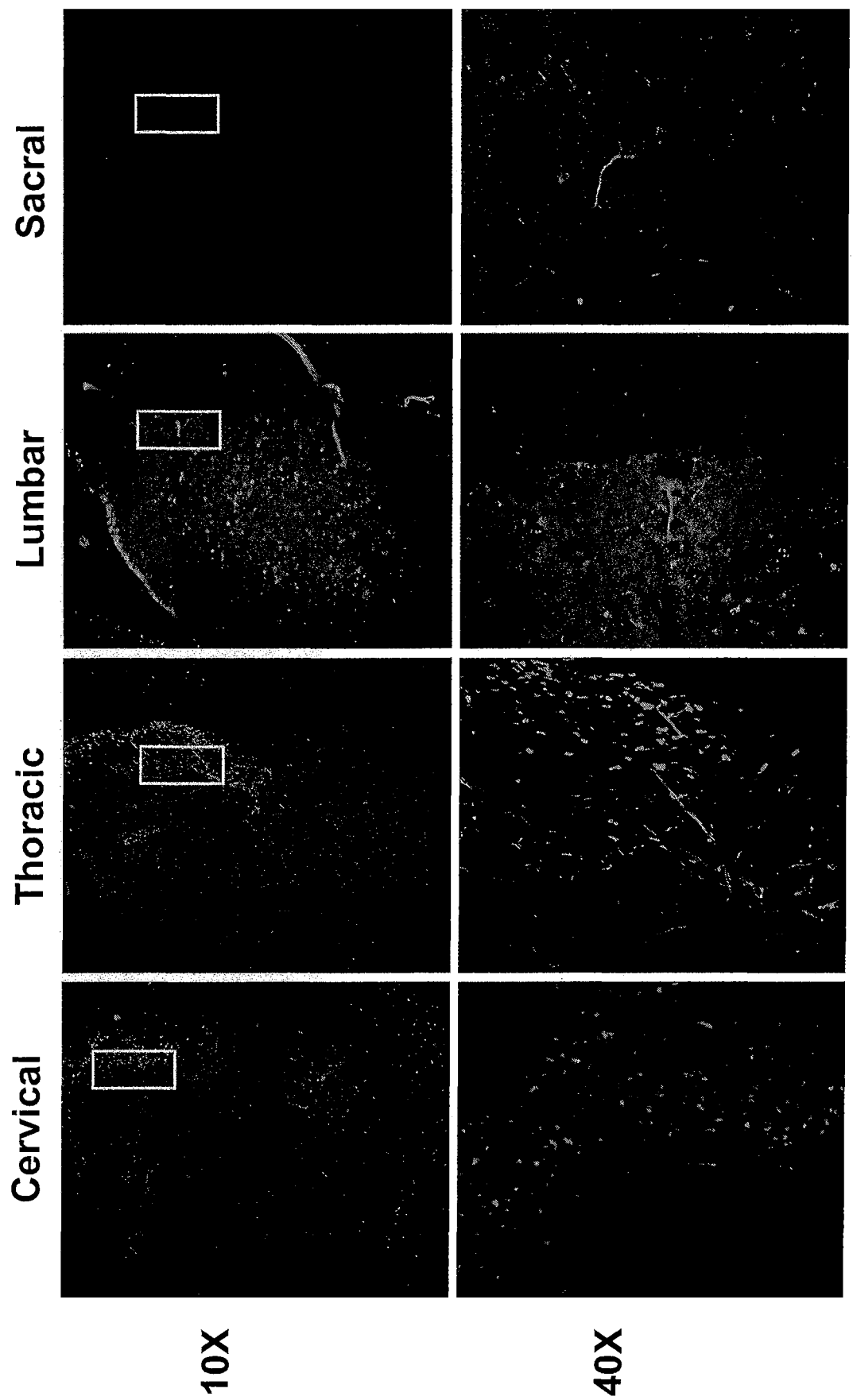
FIG. 14 illustrates green fluorescent protein distribution in the spinal cord regions following DCN delivery of AAV encoding for green fluorescent protein (GFP).
Figure 22:
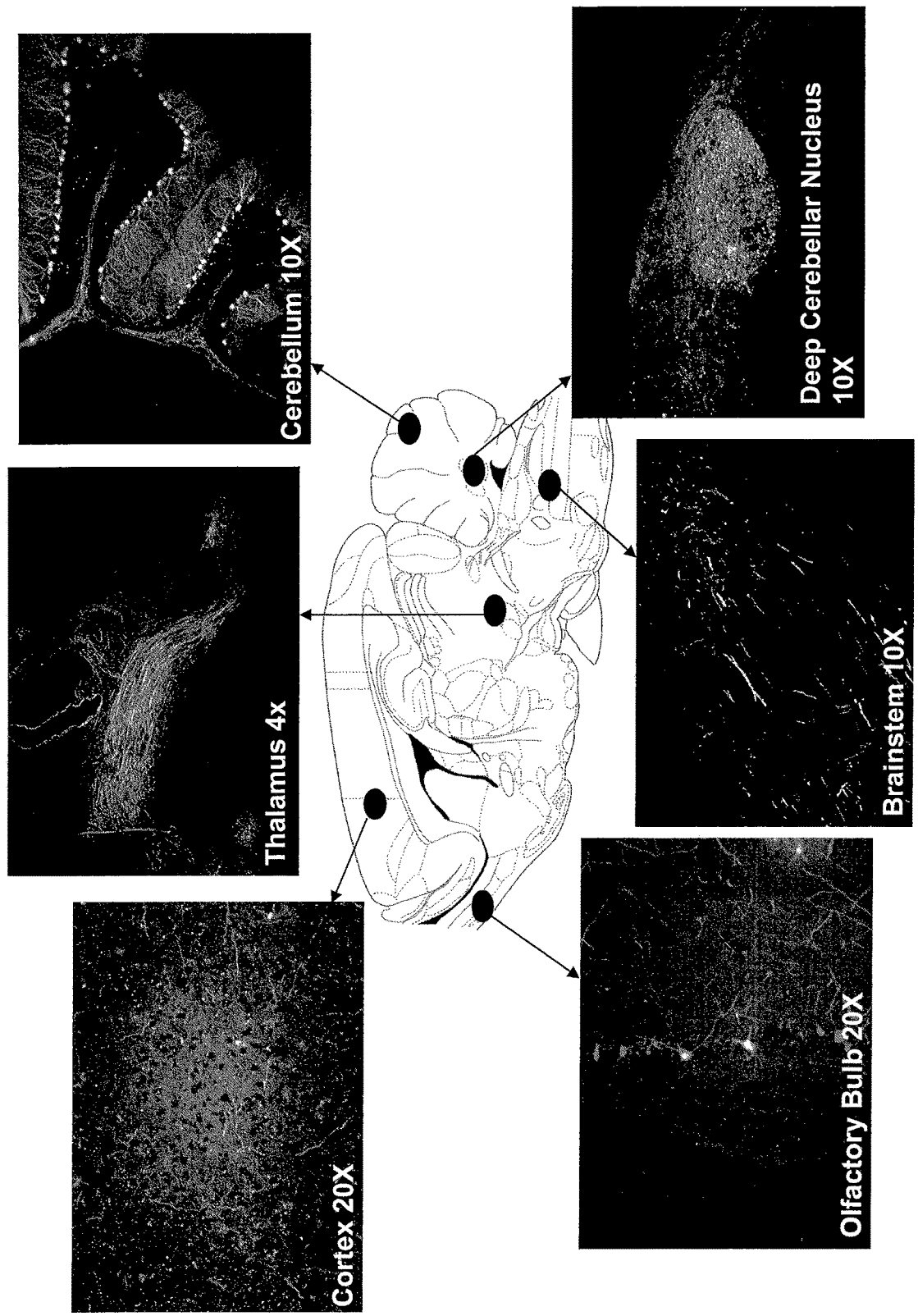
FIG. 22 shows GFP distribution within the mouse brain following bilateral delivery of a GFP expressing AAV1 vector to the deep cerebellar nuclei (DCN). In addition to the DCN, GFP positive staining was also observed in the olfactory bulbs, cerebral cortex, thalamus, brainstem, cerebellar cortex and spinal cord. All of these areas either receive projections from and/or send projections to the DCN.

GFP was detected in the brainstem and throughout each division of the spinal cord following bilateral delivery of a GFP expressing AAV vector to the deep cerebellar nuclei (DCN) (see FIGS. 13 and 14). FIG. 22 shows GFP distribution within the mouse brain. In addition to the DCN, GFP positive staining was also observed in the olfactory bulbs, cerebral cortex, thalamus, brainstem, cerebellar cortex and spinal cord. All of these areas either receive projections from and/or send projections to the DCN. In addition, GFP positive fibers and/or cells were observed in proximity to ChAT positive cells.

Figure 15:
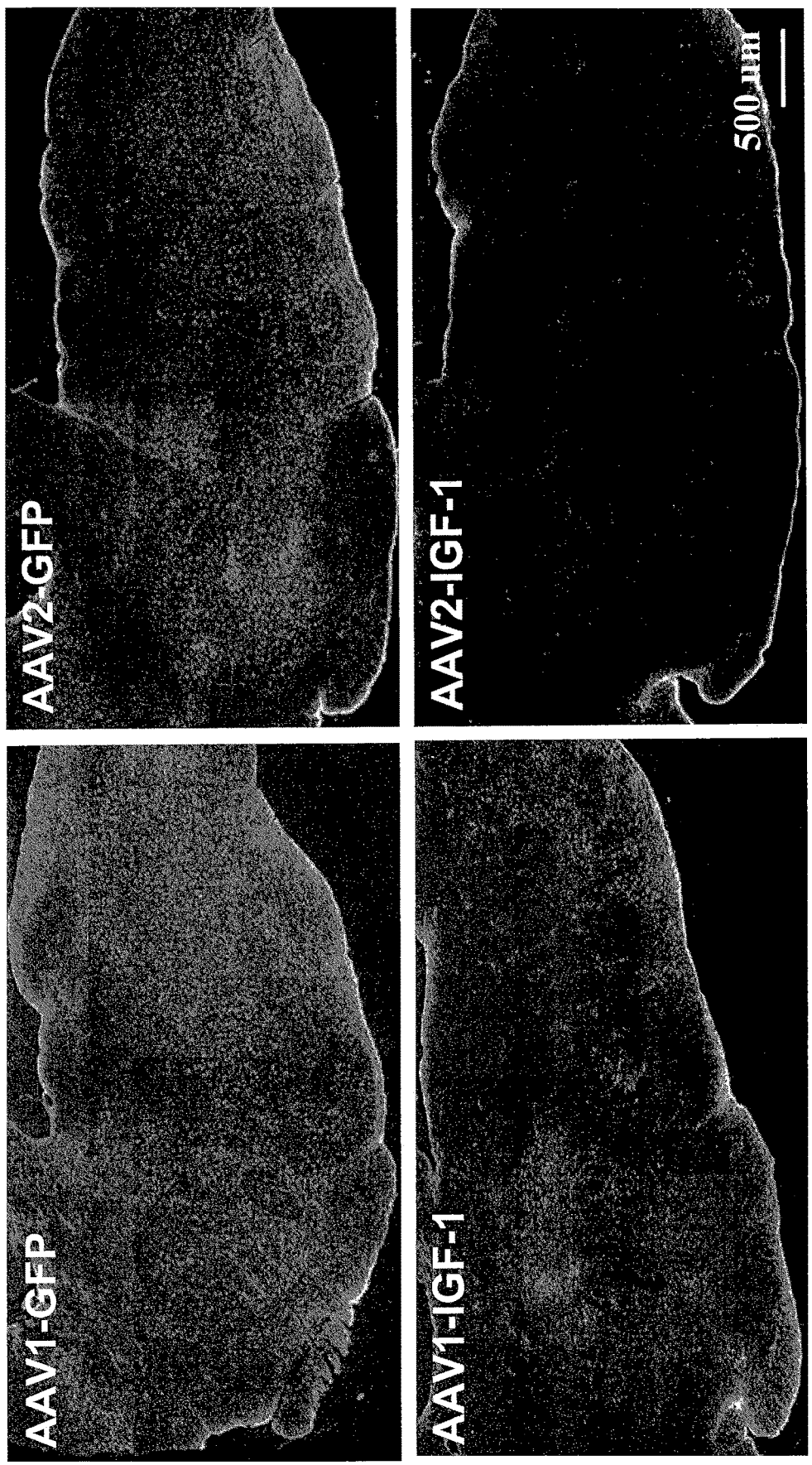
FIG. 15 illustrates the reduction in glial fibrillary acidic protein (GFAP) staining in the brainstem following DCN delivery of AAV encoding for IGF-1 as compared to DCN delivery of AAV encoding for GFP.
Figure 16:
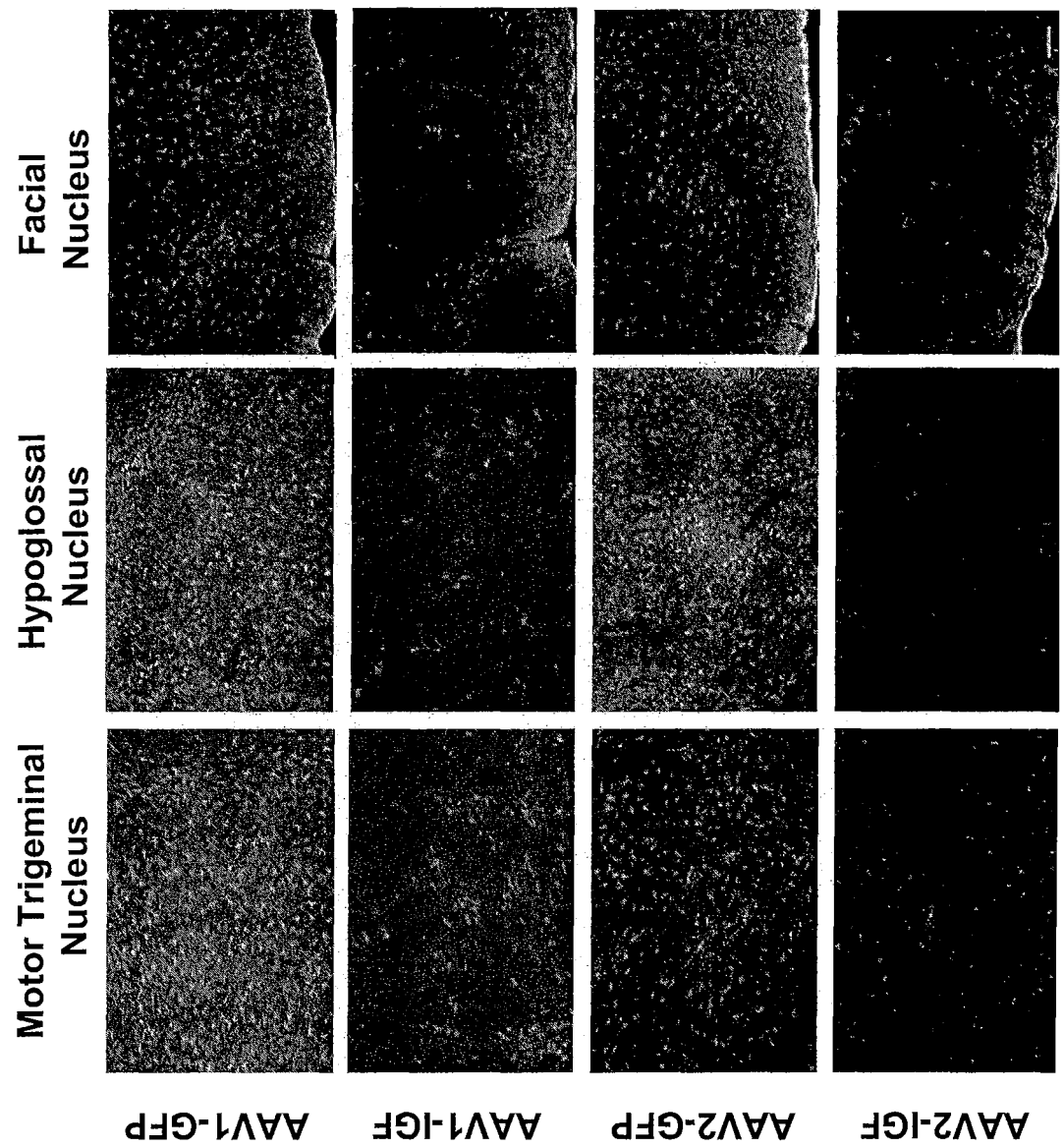
FIG. 16 illustrates the reduction in glial fibrillary acidic protein (GFAP) staining within the oromoter nuclei (trigeminal nucleus, hypoglossal nucleus, and facial nucleus) following DCN delivery of AAV encoding for IGF-1 as compared to DCN delivery of AAV encoding for GFP.
Figure 17:
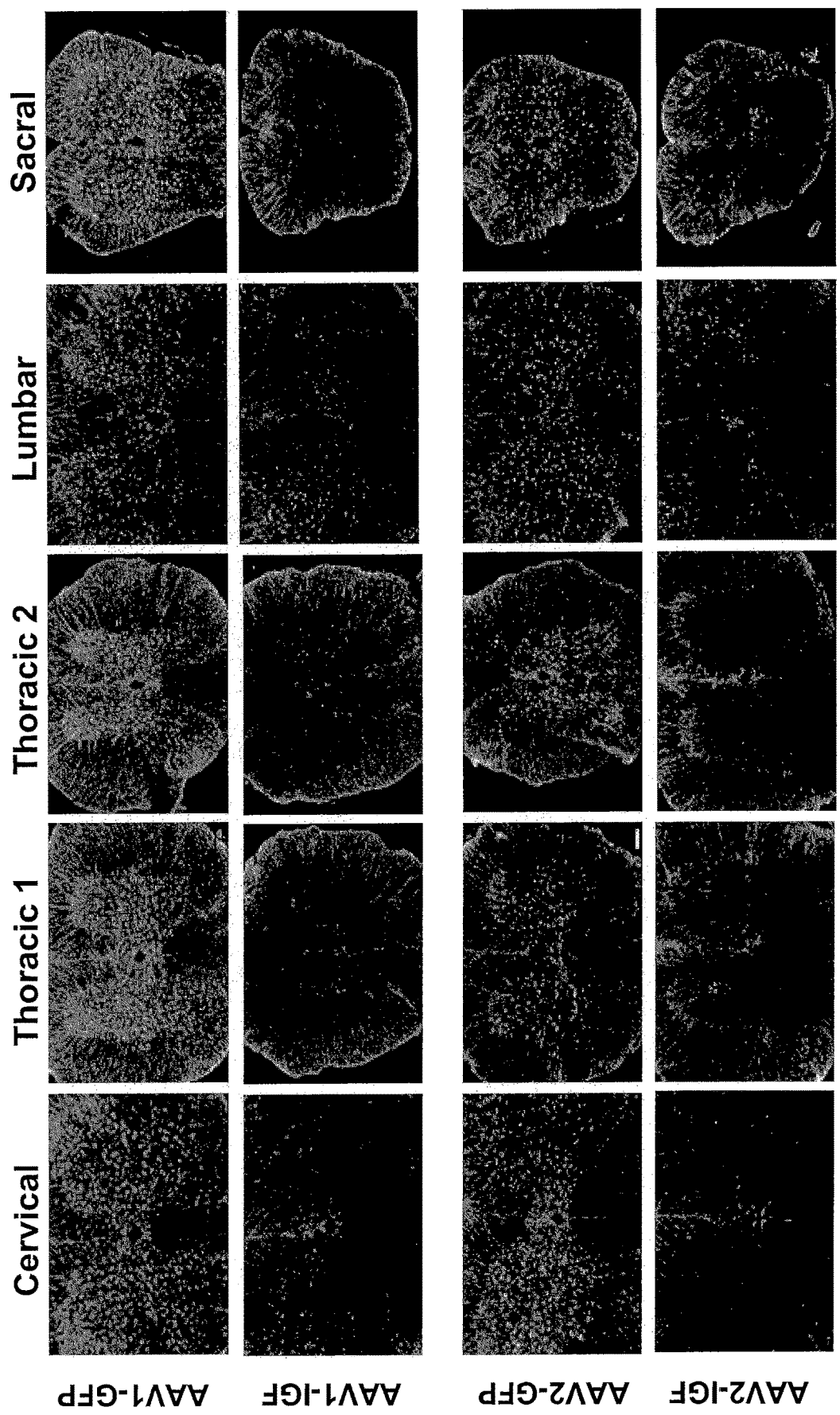
FIG. 17 illustrates the reduction in glial fibrillary acidic protein (GFAP) staining throughout the spinal cord following DCN delivery of AAV encoding for IGF-1 as compared to DCN delivery of AAV encoding for GFP.
Figure 18:
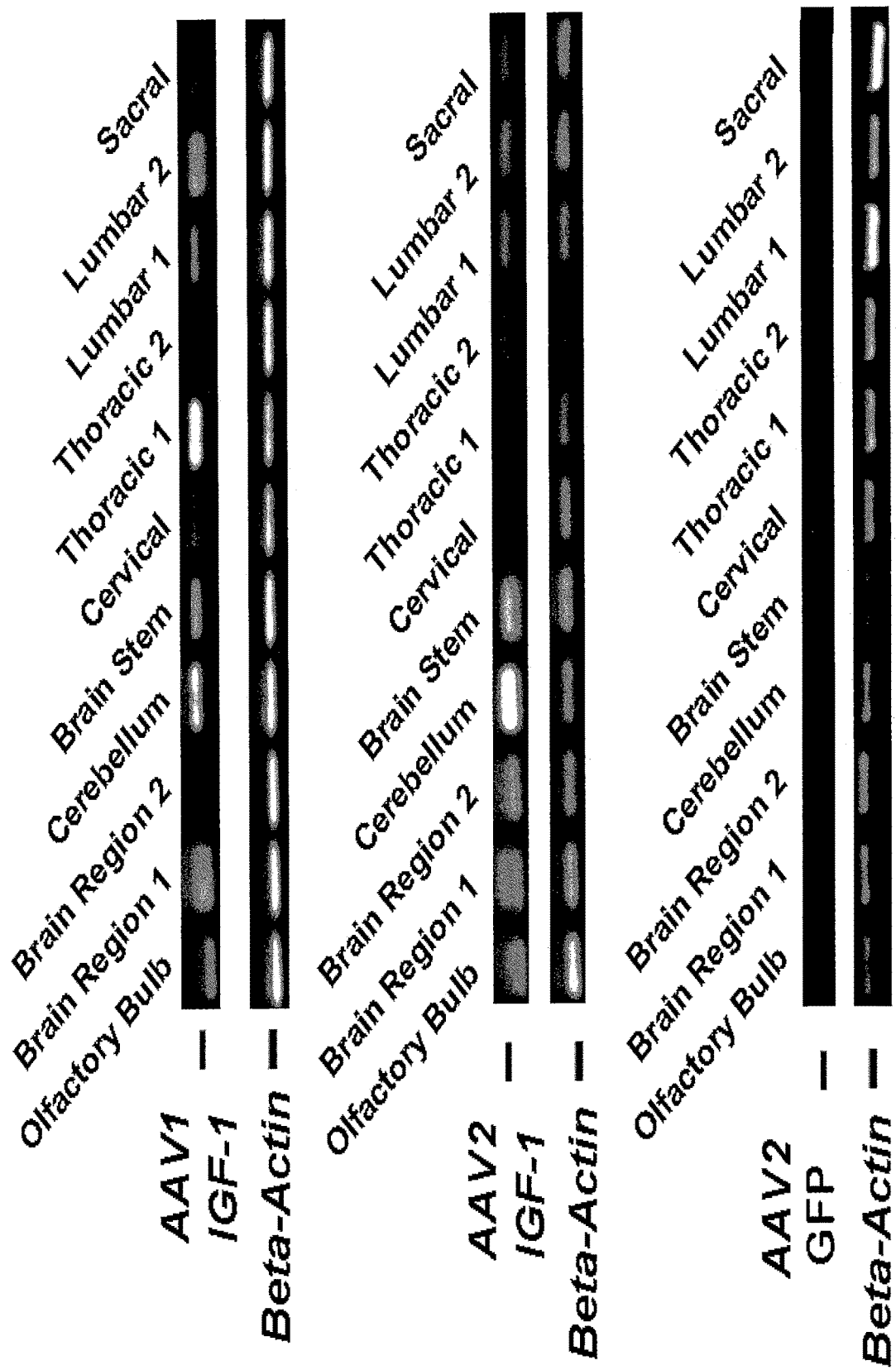
FIG. 18 illustrates the distribution of IGF-1 mRNA within the central nervous system (CNS) following DCN delivery of AAV encoding for IGF-1 as compared to DCN delivery of AAV encoding for GFP. Beta-actin is used as a positive control to compare total mRNA levels.
Figure 19:
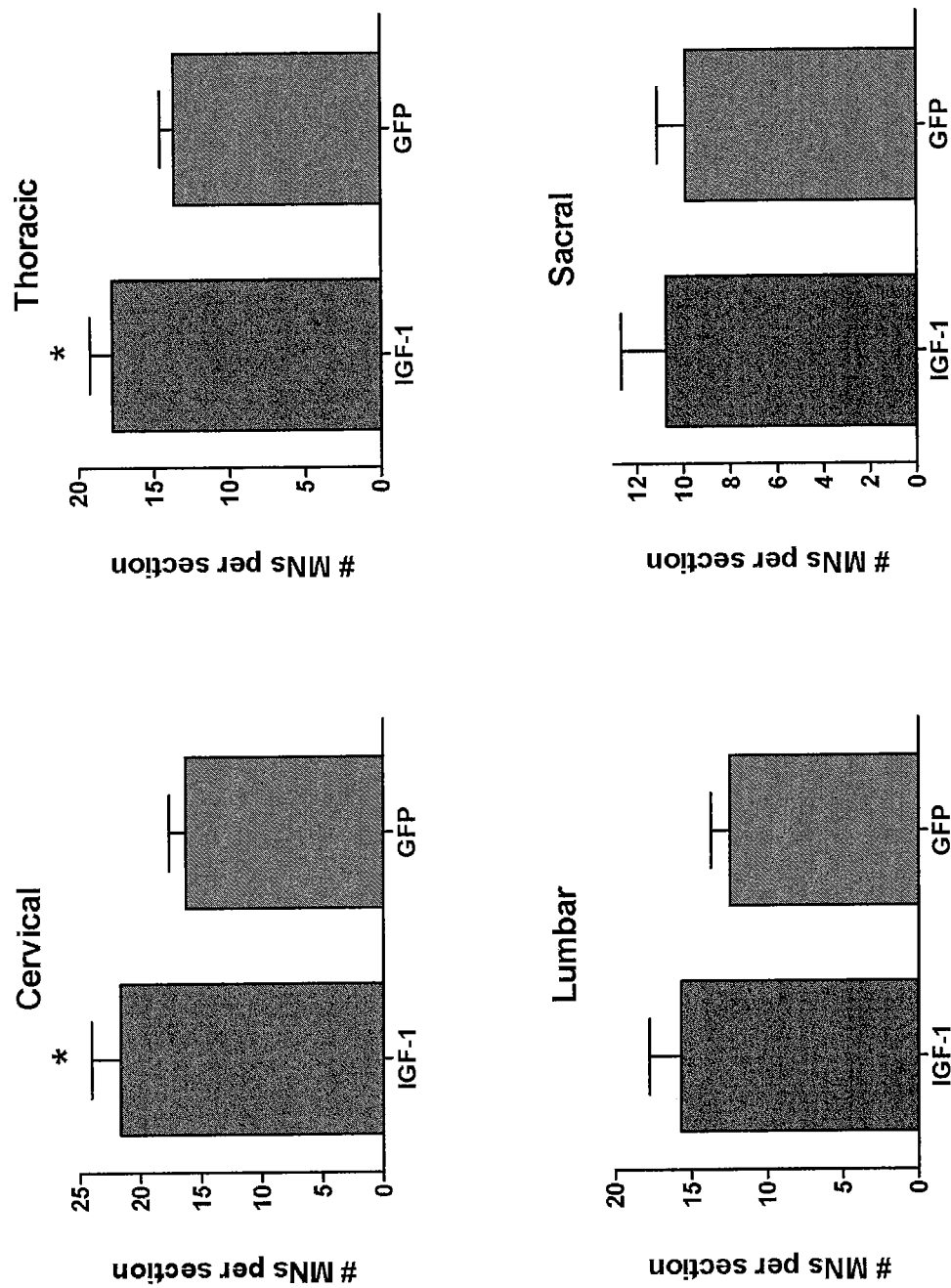
FIG. 19 illustrates that DCN delivery of AAV-IGF-1 promoted the survival of motor neurons. The difference between mice treated with AAV encoding for IGF-1 as compared to DCN delivery of AAV encoding for GFP is statistically significant to a p-value=0.01 as indicated by the asterik.
Figure 20:
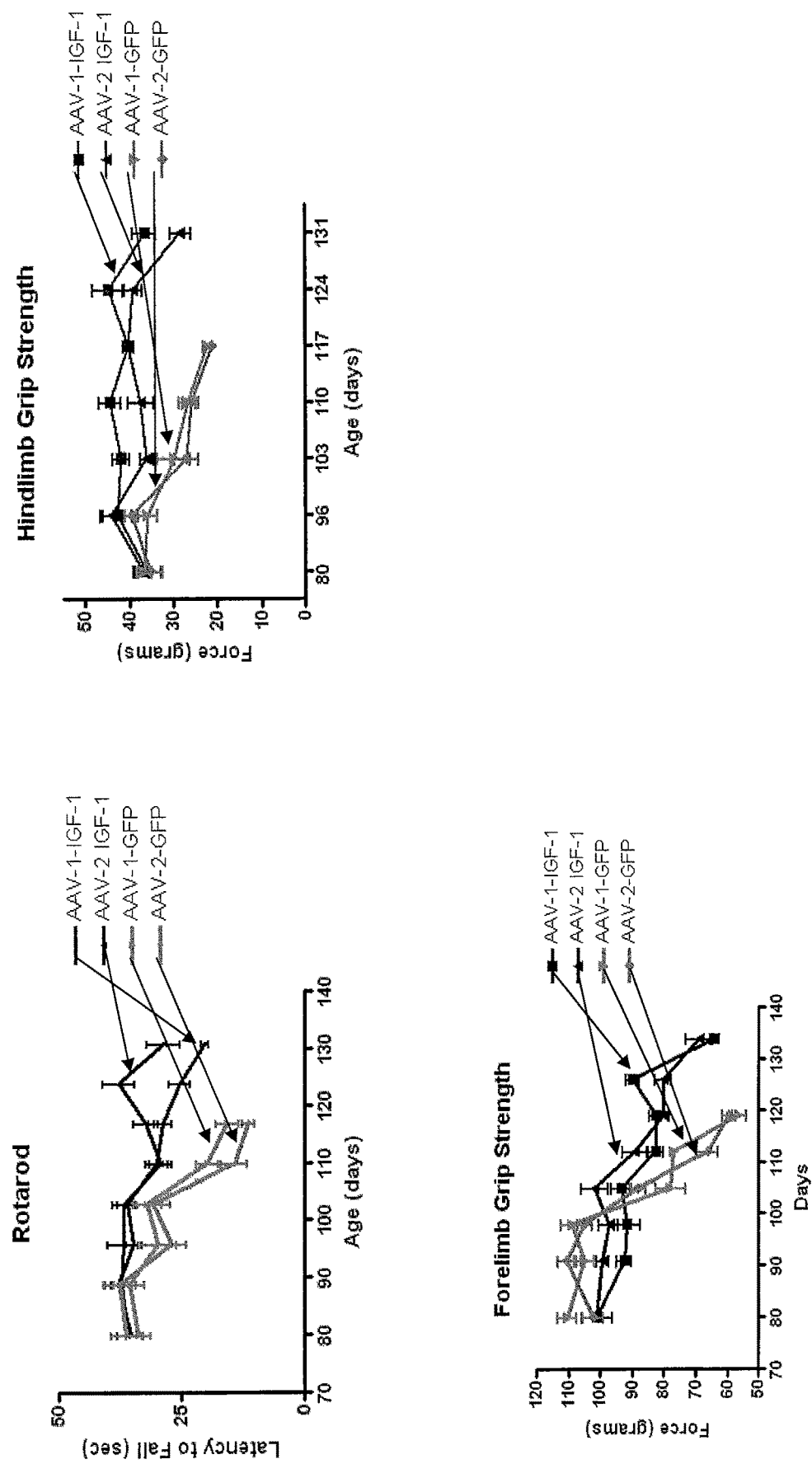
FIG. 20 illustrates the functional improvements in rotarod performance, hindlimb grip strength, and forelimb grip strength in mice treated with DCN delivery of AAV encoding for IGF-1 as compared to DCN delivery of AAV encoding for GFP.
Figure 21:
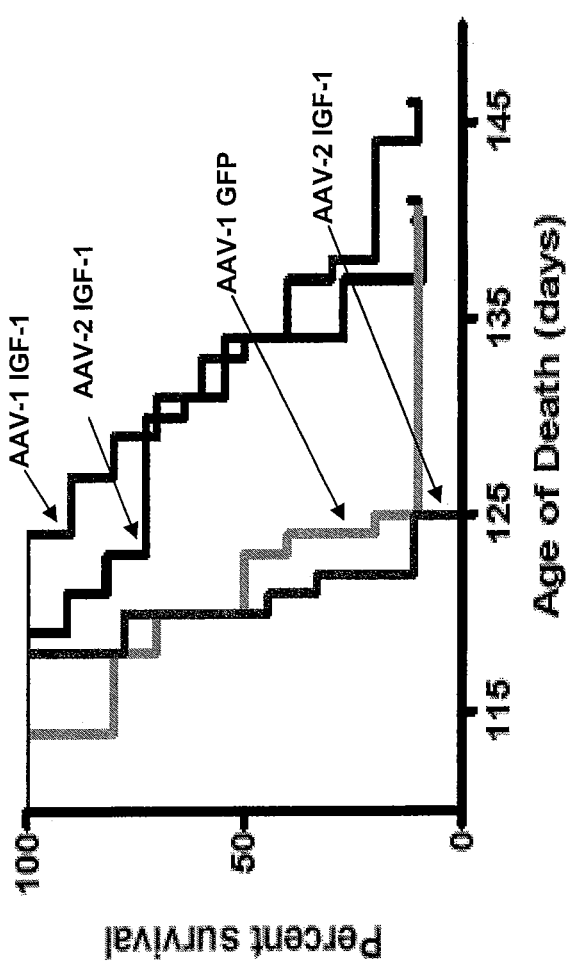
FIG. 21 illustrates the increase in survival mediated by DCN delivery of AAV encoding for IGF-1 as compared to DCN delivery of AAV encoding for GFP.

IGF-1 mRNA was detected in the brainstem and in each division of the spinal cord in mice treated with AAV1-IGF-1 or AAV2-IGF-1 demonstrating that the vector underwent retrograde transport (see FIG. 18). IGF-1 protein was detected in the brainstem and the spinal cord in mice treated with AAV1-IGF-1 or AAV2-IGF-1. A reduction in GFAP staining in the oromotor nuclei (for example, the motor trigeminal nucleus, facial nucleus, and hypoglossal nucleus) and in each division of the spinal cord was observed in mice treated with AAV1-IGF-1 or AAV2-IGF-1 (see FIGS. 15-17). GFAP is a marker of gliosis, which is a pathological hallmark of ALS. Delivery of AAV1-IGF-1 or AAV2-IGF1 led to significant functional improvement on the rotarod and grip strength tasks (see FIG. 20). Delivery of AAV-IGF-1 AAV2-IGF1 also significantly extended the lifespan of the SOD1 mouse (see FIG. 21 where median survival increased to 133.5 or 134 days in AAV-IGF-1 treated mice as compared to 121 or 120 days in AAV-GFP treated mice). FIG. 19 illustrates that DCN delivery of AAV-IGF-1 promoted the survival of motor neurons. The difference between mice treated with AAV encoding for IGF-1 as compared to DCN delivery of AAV encoding for GFP is statistically significant to a p-value=0.01 as indicated by the asterik.

Regardless of serotype, AAV-IGF-1 treatment significantly promoted motor neuron survival, improved motor performance in both rotarod and grip strength tests, and significantly extended lifespan. IGF-1 expression was detected throughout the brainstem and spinal cord using PCR and ELISA.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

REFERENCES

1. Leigh, P. N. & Swash, M. Cytoskeletal pathology in motor neuron diseases. *Adv Neurol* 56, 115-24 (1991).
2. Carpenter, S. Proximal axonal enlargement in motor neuron disease *Neurology* 18 841-51 (1968).
3. Gonatas, N. K. et al. Fragmentation of the Golgi apparatus of motor neurons in amyotrophic lateral sclerosis. *Am J Pathol* 140, 731-7 (1992).
4. Hirano, A. et al. Fine structural study of neurofibrillary changes in a family with amyotrophic lateral sclerosis. *J Neuropathol Exp Neurol* 43, 471-80 (1984).
5. Leigh, P. N. et al. Ubiquitin-immunoreactive intraneuronal inclusions in amyotrophic lateral sclerosis. Morphology, distribution, and specificity. *Brain* 114 (Pt 2), 775-88 (1991).
6. Delisle, M. B. & Carpenter, S, Neurofibrillary axonal swellings and amyotrophic lateral sclerosis. *J Neurol Sci* 63, 241-50 (1984).
7. Hirano, A. Neuropathology of ALS: an overview. *Neurology* 47, S63-6 (1996).
8. Rosen, D. R. et al. Mutations in Cu/Zn superoxide dismutase gene are associated with familial amyotrophic lateral sclerosis. *Nature* 362, 59-62 (1993).
9. Gurney, M. E. et al. Motor neuron degeneration in mice that express a human Cu,Zn superoxide dismutase mutation. *Science* 264, 1772-5 (1994).
10. Rowland, L. P. & Shneider, N. A. Amyotrophic lateral sclerosis. *N Engl J Med* 344, 1688-700 (2001).
11. Bruijn, L. I., Miller, T. M. & Cleveland, D. W. Unraveling the mechanisms involved in motor neuron degeneration in ALS. *Annu Rev Neurosci* 27, 723-49 (2004).

12. Cleveland, D. W. & Rothstein, J. D. From Charcot to Lou Gehrig: deciphering selective motor neuron death in ALS. *Nat Rev Neurosci* 2, 806-19 (2001).
13. Lindsay, R. M. Neurotrophic growth factors and neurodegenerative diseases: therapeutic potential of the neurotrophins and ciliary neurotrophic factor. *Neurobiol Aging* 15, 249-51 (1994).
14. Kaspar, B. K., Llado, J., Sherkat, N., Rothstein, J. D. & Gage, F. H. Retrograde viral delivery of IGF-1 prolongs survival in a mouse ALS model. *Science* 301, 839-42 (2003).
15. Clement, A. M. et al. Wild-type nonneuronal cells extend survival of SOD1 mutant motor neurons in ALS mice. *Science* 302, 113-7 (2003).
16. Matsushita, M. Projections from the lowest lumbar and sacral-caudal segments to the cerebellar nuclei in the rat, studied by anterograde axonal tracing. *J Comp Neurol* 404, 21-32 (1999).
17. Matsushita, M. & Gao, X. Projections from the thoracic cord to the cerebellar nuclei in the rat, studied by anterograde axonal tracing. *J Comp Neurol* 386, 409-21 (1997).
18. Matsushita, M. & Xiong, G. Projections from the cervical enlargement to the cerebellar nuclei in the rat, studied by anterograde axonal tracing. *J Comp Neurol* 377, 251-61 (1997).
19. Matsushita, M. & Yaginuma, H. Afferents to the cerebellar nuclei from the cervical enlargement in the rat, as demonstrated with the *Phaseolus vulgaris* leucoagglutinin method. *Neurosci Lett* 113, 253-9 (1990).
20. Matsushita, M. & Yaginuma, H. Projections from the central cervical nucleus to the cerebellar nuclei in the rat, studied by anterograde axonal tracing. *J Comp Neurol* 353, 234-46 (1995); Voogd, J. The cerebellar nuclei and their efferent pathways. in *The rat nervous system* (ed. Paxinos, G.) 208-215 (Elsevier Academic Press, San Diego, 2004).

The invention claimed is:

1. A method to treat amyotrophic lateral sclerosis (ALS) in a subject, comprising administering a recombinant neurotropic viral vector comprising a therapeutic transgene to at least one region of the deep cerebellar nuclei region of the brain under conditions that favor expression of the transgene in a motor neuron distal to the site of administration, wherein the transgene product is delivered in a therapeutically effective amount to at least one subdivision of the spinal cord and/or at least one division of the brainstem, wherein said neurotropic viral vector is an adeno-associated viral vector comprising an AAV1 serotype capsid, and wherein the therapeutic transgene is insulin growth factor-1 (IGF-1).

2. The method of claim 1, wherein said region of the deep cerebellar nuclei region of the brain is selected from the group consisting of the medial region, interposed region and the lateral region.

3. The method of claim 1, wherein said delivery is bilateral.

4. The method of claim 1, wherein said spinal cord subdivision is selected from the group consisting of the cervical subdivision, the thoracic subdivision, the lumbar subdivision, and the sacral subdivision.

5. The method of claim 1, wherein said transgene product is delivered to all subdivisions of the spinal cord.

6. The method of claim 1, wherein the administration comprises multiple administrations.

7. The method of claim 1, wherein said subject is a human patient.

8. The method of claim 1, wherein said transgene expresses a therapeutic amount of insulin growth factor-1 (IGF-1).

9. The method of claim 1, wherein the AAV vector comprises an AAV2 ITR or an AAV1 ITR.

10. The method of claim 6, wherein at least one of the multiple administrations is bilateral.

* * * * *

UNITED STATES PATENT AND TRADEMARK OFFICE
CERTIFICATE OF CORRECTION

PATENT NO. : 10,744,210 B2
APPLICATION NO. : 11/934148
DATED : August 18, 2020
INVENTOR(S) : Dodge et al.

It is certified that error appears in the above-identified patent and that said Letters Patent is hereby corrected as shown below:

On the Title Page

Item (75) Inventors, Line 4 replace "Wellesley, MA" with --Natick, MA--.

Signed and Sealed this
Tenth Day of May, 2022

Katherine Kelly Vidal
*Director of the United States Patent and Trademark Office*